(12) United States Patent
Haber et al.

(10) Patent No.: US 9,766,244 B2
(45) Date of Patent: Sep. 19, 2017

(54) DIAGNOSIS AND MONITORING TREATMENT OF PROSTATE CANCER

(71) Applicant: THE GENERAL HOSPITAL CORPORATION, Boston, MA (US)

(72) Inventors: Daniel A. Haber, Newton, MA (US); Shyamala Maheswaran, Lexington, MA (US); David T. Miyamoto, Wellesley, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 14/412,235

(22) PCT Filed: Jul. 1, 2013

(86) PCT No.: PCT/US2013/048863
§ 371 (c)(1),
(2) Date: Dec. 31, 2014

(87) PCT Pub. No.: WO2014/008155
PCT Pub. Date: Jan. 9, 2014

(65) Prior Publication Data
US 2015/0168413 A1   Jun. 18, 2015

Related U.S. Application Data

(60) Provisional application No. 61/667,040, filed on Jul. 2, 2012.

(51) Int. Cl.
*A61K 39/00* (2006.01)
*G01N 33/574* (2006.01)
*A61K 31/167* (2006.01)
*A61K 31/496* (2006.01)
*A61K 31/58* (2006.01)
*C12Q 1/68* (2006.01)

(52) U.S. Cl.
CPC ..... *G01N 33/57434* (2013.01); *A61K 31/167* (2013.01); *A61K 31/496* (2013.01); *A61K 31/58* (2013.01); *C12Q 1/6886* (2013.01); *A61K 2039/505* (2013.01); *C12Q 2600/106* (2013.01); *C12Q 2600/112* (2013.01); *G01N 2333/705* (2013.01)

(58) Field of Classification Search
CPC .............................................. A61K 2039/505
See application file for complete search history.

(56) References Cited

FOREIGN PATENT DOCUMENTS

WO    2011/127219 A1    10/2011

OTHER PUBLICATIONS

Jemaa et al. (J. Immunoassay Immunochem. 2014; 35 (1): 48-59).*
Morgan et al. (Clin. Cancer Res. Jan. 15, 2009; 15 (2): 677-83).*
Pilepich et al. (Int. J. Radiat. Oncol. Biol. Phys. Apr. 1, 2005; 61 (5): 1285-90).*
Elgamal et al. (Semin. Surg. Oncol. Jan.-Feb. 2000; 18 (1): 10-6).*
Yates et al. (Prostate. Sep. 1, 2012; 72 (12): 1382-8).*
Miyamoto et al. (Cancer Discov. Nov. 2012; 2 (11): 995-1003).*
De Bono et al., "Abiraterone and Increased Survival in Metastatic Prostate Cancer", N. Engl. J. Med. 364 (21):1995-2005 (2011).
Evans et al., "Noninvasive measurement of androgen receptor signaling with a positron-emitting radiopharmaceutical that targets prostate-specific membrane antigen", PNAS 108(23):9578-9582 (2011).
Miyamoto et al., "Androgen Receptor Signaling in Circulating Tumor Cells as a Marker of Hormonally Responsive Prostate Cancer", Cancer Discovery 2(11):995-1003 (2012).
Ozkumur et al., "Inertial Focusing for Tumor Antigen-Dependent and -Independent Sorting of Rare Circulating Tumor Cells", Sci. Transl. Med. 5(179):179ra47 (2013).
Scher et al., "Biology of Progressive, Castration-Resistant Prostate Cancer: Directed Therapies Targeting the Androgen-Receptor Signaling Axis", J. Clin. Oncol. 23(32):8253-8261 (2005).
Scher et al., "Design and End Points of Clinical Trials for Patients with Progressive Prostate Cancer and Castrate Levels of Testosterone: Recommendations of the Prostate Cancer Clinical Trials Working Group", J. Clin. Oncol. 26 (7):1148-1159 (2008).
Stott et al., "Isolation and Characterization of Circulating Tumor Cells from Patients with Localized and Metastatic Prostate Cancer", Sci. Transl. Med. 2(25):25ra23 (2010).
Stott et al., "Isolation of circulating tumor cells using a microvortex-generating herringbone-chip", PNAS 107 (43):18392-18397 (2010).
Ulmert et al., "Imaging Androgen Receptor Signaling with a Radiotracer Targeting Free Prostate-Specific Antigen", Cancer Discov. 2(4):320-327 (2012).
Yuan et al., "Mechanisms Mediating Androgen Receptor Reactivation After Castration", 27(1):36-41 (2009).
Gleghorn et al., Lab Chip. 10(1):27-29 (2010). "Capture of circulating tumor cells from whole blood of prostate cancer patients using geometrically-enhanced differential immunocapture (GEDI) and a prostate specific antibody."
Panteleakou et al., Mol Med. 15(3-4):101-114 (2009). "Detection of circulating tumor cells in prostate cancer patients: Methodological pitfalls and clinical relevance."

* cited by examiner

*Primary Examiner* — Stephen Rawlings
(74) *Attorney, Agent, or Firm* — Nixon Peabody LLP; Mark J. FitzGerald; David S. Resnick

(57) ABSTRACT

Provided herein are assays and methods related to determining a ratio of expression levels of PSA/PSMA or determining the expression level of PSMA in circulating tumor cells for diagnosis and/or for the purpose of monitoring treatment efficacy for prostate cancers that are likely hormone resistant.

8 Claims, 10 Drawing Sheets

3A

3B

FIGs. 4A-4G
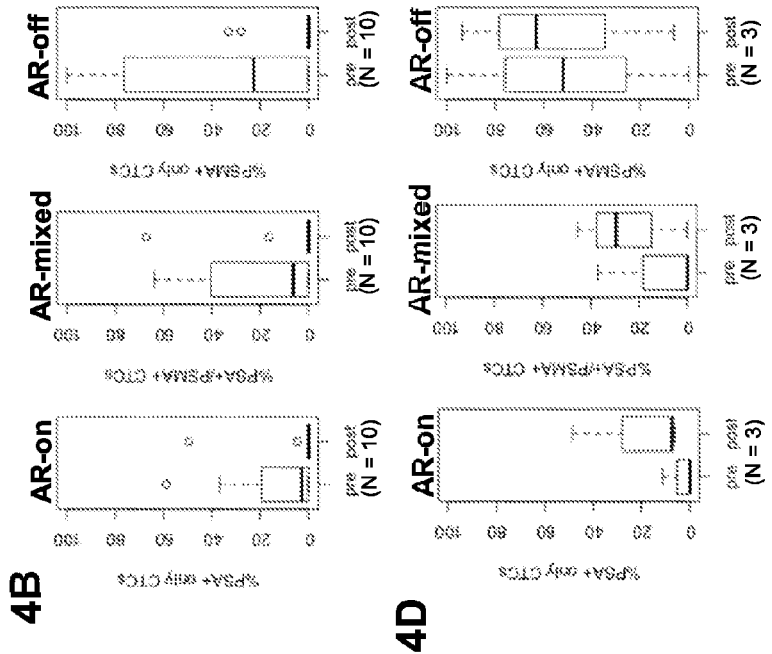
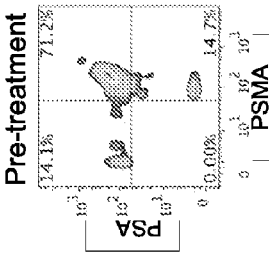
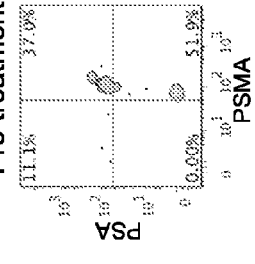

DIAGNOSIS AND MONITORING TREATMENT OF PROSTATE CANCER

CROSS REFERENCE TO RELATED APPLICATIONS

This application is a 35 U.S.C. §371 National Stage Application of International Application No. PCT/US2013/048863 filed on Jul. 1, 2013, which designates the United States, and which claims benefit under 35 U.S.C. §119(e) of U.S. Provisional Application No. 61/667,040 filed Jul. 2, 2012, the content of which is incorporated herein by reference in its entirety.

GOVERNMENT SUPPORT

The present application was made with Government support under Grant Number 5R01EB008047 awarded by National Institute of Biomedical Imaging and Bioengineering, National Institutes of Health. The Government of the United States has certain rights in the invention.

FIELD OF THE INVENTION

The field of the invention relates to the diagnosis and treatment of prostate cancer.

BACKGROUND

Prostate cancer is the most commonly diagnosed malignant cancer in males in the United States and is the second leading cause of male cancer mortality. Surgery and/or radiation therapies can be employed to treat prostate cancer and further to prevent progression of the disease. However, in some cases systemic therapy based on inhibiting the androgen receptor (AR) is employed.

The androgen receptor is a steroid receptor transcription factor which promotes the growth and survival of both normal and cancerous prostate cells. Androgen ablation is used to block the activation or activity of androgens initially and often results in a favorable clinical response. However, prostate cancer can continue to progress and becomes resistant to androgen ablation, a disease status referred to as "castration-resistant prostate cancer."

Clinical findings demonstrate that a majority of castration-resistant prostate cancers still express AR and androgen-dependent genes, indicating that the AR-signaling pathway is functional in the absence of androgens or in the presence of low levels of androgens (Chang, C. S. et al., *Science* 240, 324-6 (1988); Lubahn, D. B. et al., *Mol Endocrinol* 2, 1265-75 (1988)). Several independent studies have also shown that AR is essential for both hormone sensitive and recurrent hormone refractory prostate cancer (McPhaul, M. J. et al., *J Investig Dermatol Symp Proc* 8, 1-5 (2003); Heinlein, C. A. et al., *Endocr Rev* 25, 276-308 (2004)). Mutations and amplification of AR, alterations in protein kinases, growth factors and nuclear receptor coactivators have all been proposed to modulate AR signaling and may, therefore, play key roles in the development of androgen independence of prostate cancer (Feldman, B. et al., *Nat Rev Cancer* 1, 34-45 (2001); Lubahn, D. B. et al. *Mol Endocrinol* 2, 1265-75 (1988); Kuiper, G. G. et al., *J Mol Endocrinol* 2, R1-4 (1989)). Increased AR expression level has also been shown to associate with the development of resistance to anti-androgen therapy (McPhaul, M. J. et al., J Investig Dermatol Symp Proc 8, 1-5 (2003)).

SUMMARY

The methods and assays disclosed herein are based, in part, on the discovery that an increase in the ratio of expression levels of prostate specific antigen (PSA) to prostate-specific membrane antigen (PSMA) measured in circulating tumor cells is predictive of the emergence of hormone therapy-resistant or castration-resistant prostate cancer. The ratio of PSA/PSMA expression levels in circulating tumor cells can also be used to monitor treatment efficacy of an agent for treating prostate cancer, for example, a hormone therapy such as leuprolide. If the PSA/PSMA expression levels begin to rise during a course of such treatment, one can predict that the prostate cancer is no longer responding to the present treatment strategy (e.g., an anti-hormone therapy) and thus the treatment can be discontinued in favor of a treatment strategy with a different therapy, e.g., one that has not been previously administered and/or targets another tumor growth pathway. A reduction in PSA/PSMA ratios in circulating tumor cells (CTCs) compared to a reference standard can indicate that the androgen pathway is active and/or not hormone independent, and the patient is more likely to respond to second line hormonal agents (e.g., abiratorone or others), whereas if the androgen pathway is inactive and/or hormone independent in CTCs (predicted by an increased ratio of PSA/PSMA), then the patient may need chemotherapy or other types of non-hormonal therapies. Monitoring the PSA/PSMA ratio permits the ordinary skilled physician to predict changes in hormone dependency and to alter the treatment at an earlier time point than otherwise achievable, thereby selecting an efficacious treatment and permitting the treatment to be implemented earlier than if the physician were to monitor accepted clinical signs alone. For example, the methods and assays provided herein are particularly effective for when a patient is not likely to continue to respond to leuprolide and other first-line hormonal therapies and it will be necessary to select or monitor efficacy of a second-line hormonal therapy or a chemotherapeutic agent. Thus, provided herein are assays and methods for determining a ratio of expression levels of prostate specific antigen (PSA) and PSMA in circulating tumor cells for diagnosis and/or monitoring treatment efficacy for prostate cancers that may or may not respond to hormone therapies.

Also provided herein are assays and methods for detecting PSMA expression levels, wherein a decrease in PSMA expression in CTC is an indicator of a progression of prostate cancer, e.g., towards prostate cancers that do not respond to hormone therapies. The level of PSMA in CTCs can also be serially monitored to determine whether an individual determined to have a hormone-resistant prostate cancer is responsive to a particular treatment.

One aspect described herein relates to an assay comprising (a) determining the ratio of expression levels of prostate specific antigen (PSA) to prostate specific membrane antigen (PSMA) in circulating tumor cells isolated from a biological sample obtained from a subject determined to have prostate cancer, (b) comparing the ratio of expression levels determined in step (a) to a reference value, and if the ratio is increased relative to the reference value identifying the subject as being unlikely to respond to hormonal therapy, and if the ratio is the same or reduced relative to the reference value identifying the subject as likely to respond to hormonal therapy.

In one embodiment of this aspect and all other aspects described herein, the biological sample obtained from a subject comprises a blood sample.

In another embodiment of this aspect and all other aspects described herein, the reference value is obtained from a subject or population of subjects with prostate cancer.

In another embodiment of this aspect and all other aspects described herein, the reference value is obtained from the same subject at an earlier time point.

In another embodiment of this aspect and all other aspects described herein, the circulating tumor cells are isolated using a microfluidic capture method.

In another embodiment of this aspect and all other aspects described herein, the prostate cancer is metastatic prostate cancer.

In another embodiment of this aspect and all other aspects described herein, the subject was previously being treated with a hormone therapy for prostate cancer, or is currently being treated with a hormone therapy for prostate cancer.

In another embodiment of this aspect and all other aspects described herein, the hormone therapy for prostate cancer comprises leuprolide.

In another embodiment of this aspect and all other aspects described herein, the expression levels of PSA and PSMA are determined by contacting the isolated circulating tumor cells with antibody reagents specific for PSA and PSMA.

In another embodiment of this aspect and all other aspects described herein, the RNA expression levels of PSA and PSMA are determined at the single cell level using an in situ RNA hybridization assay. In another embodiment of this aspect and all other aspects described herein, the RNA expression levels of PSA and PSMA are determined at the single cell level using a qRT-PCR assay.

In another embodiment of this aspect and all other aspects described herein, the expression levels of PSA and PSMA are determined by immunofluorescence staining and/or automated fluorescence microscopy.

Another aspect described herein relates to an assay comprising: (a) determining the ratio of expression levels of prostate specific antigen (PSA) to prostate specific membrane antigen (PSMA) in circulating tumor cells isolated from a biological sample obtained from a subject undergoing treatment for prostate cancer, (b) comparing the ratio of expression levels determined in step (a) to a reference value, wherein if the ratio determined in step (a) is reduced relative to the reference value, identifying the subject as responding to the treatment.

In one embodiment of this aspect and all other aspects described herein, the reference value comprises a ratio of expression levels determined in the subject or a population of subjects prior to initiation of the treatment for prostate cancer.

In another embodiment of this aspect and all other aspects described herein, the reference value comprises a ratio of expression levels determined in a population of subjects determined to have castration-resistant prostate cancer.

In another embodiment of this aspect and all other aspects described herein, the biological sample obtained from a subject comprises a blood sample.

In another embodiment of this aspect and all other aspects described herein, the prostate cancer is metastatic prostate cancer.

In another embodiment of this aspect and all other aspects described herein, the treatment for prostate cancer comprises leuprolide.

In another embodiment of this aspect and all other aspects described herein, the circulating tumor cells are isolated using a microfluidic capture method.

In another embodiment of this aspect and all other aspects described herein, the expression levels of PSA and PSMA are determined by contacting the isolated circulating tumor cells with antibody reagents specific for PSA and PSMA.

In another embodiment of this aspect and all other aspects described herein, the RNA expression levels of PSA and PSMA are determined at the single cell level using an in situ RNA hybridization assay. In another embodiment of this aspect and all other aspects described herein, the RNA expression levels of PSA and PSMA are determined at the single cell level using a qRT-PCR assay.

In another embodiment of this aspect and all other aspects described herein, the expression levels of PSA and PSMA are determined by immunofluorescence staining and/or automated fluorescence microscopy.

In another embodiment of this aspect and all other aspects described herein, the subject is being treated with bicalutamide, MVD3100, abiraterone acetate, cabazitaxel, sipulecel T, ketoconazole, TAK-700, or a taxane chemotherapeutic agent.

Also provided herein, in another aspect, is an assay comprising: (a) isolating circulating tumor cells (CTCs) from a blood sample obtained from a subject undergoing treatment for prostate cancer, (b) measuring the level of expression of prostate specific antigen (PSA) and prostate specific membrane antigen (PSMA) in isolated CTCs, (c) determining the ratio of expression of PSA/PSMA, and (d) comparing the ratio of expression of PSA/PSMA to a reference value, wherein if the ratio determined in step (a) is reduced relative to the reference value, identifying the subject as responding to the treatment.

In one embodiment of this aspect and all other aspects described herein, the reference value comprises a ratio of expression levels determined in the subject or a population of subjects prior to initiation of the treatment for prostate cancer.

In another embodiment of this aspect and all other aspects described herein, the reference value comprises a ratio of expression levels determined in a population of subjects determined to have castration-resistant prostate cancer.

In another embodiment of this aspect and all other aspects described herein, the biological sample obtained from a subject comprises a blood sample.

In another embodiment of this aspect and all other aspects described herein, the circulating tumor cells are isolated using a microfluidic capture method.

In another embodiment of this aspect and all other aspects described herein, the expression levels of PSA and PSMA are determined by contacting the isolated circulating tumor cells with antibody reagents specific for PSA and PSMA.

In another embodiment of this aspect and all other aspects described herein, the RNA expression levels of PSA and PSMA are determined at the single cell level using an in situ RNA hybridization assay. In another embodiment of this aspect and all other aspects described herein, the RNA expression levels of PSA and PSMA are determined at the single cell level using a qRT-PCR assay.

In another embodiment of this aspect and all other aspects described herein, the expression levels of PSA and PSMA are determined by immunofluorescence staining and/or automated fluorescence microscopy.

In another embodiment of this aspect and all other aspects described herein, the subject is being treated with bicalutamide, MVD3100, abiraterone acetate, cabazitaxel, sipulecel T, ketoconazole, TAK-700, or a taxane chemotherapeutic agent.

Another aspect described herein relates to a method of treating a patient determined to have prostate cancer, the method comprising: administering to a patient determined to have a ratio of prostate specific antigen (PSA) to prostate specific membrane antigen (PSMA) expression in isolated circulating tumor cells that is increased compared to that of a reference value, a pharmaceutically effective amount of a prostate cancer agent that has not been previously administered to the patient.

In one embodiment of this aspect and all other aspects described herein, the prostate cancer agent that has not been previously administered is bicalutamide, MVD3100, abiraterone acetate, cabazitaxel, sipulecel T, ketoconazole, TAK-700, or a taxane chemotherapeutic agent.

In another embodiment of this aspect and all other aspects described herein, the subject is currently undergoing treatment with a hormone therapy for prostate cancer, or was previously treated with a hormone therapy for prostate cancer.

In another embodiment of this aspect and all other aspects described herein, the hormone therapy comprises leuprolide.

In another embodiment of this aspect and all other aspects described herein, the hormone therapy is discontinued prior to treatment with the anti-cancer agent.

In another embodiment of this aspect and all other aspects described herein, the reference value is obtained from a subject or population of subjects having prostate cancer.

In another embodiment of this aspect and all other aspects described herein, the circulating tumor cells are isolated using a microfluidic capture method.

In another embodiment of this aspect and all other aspects described herein, the circulating tumor cells are isolated from a blood sample obtained from the subject.

In another embodiment of this aspect and all other aspects described herein, the expression levels of PSA and PSMA are determined by contacting the isolated circulating tumor cells with antibody reagents specific for PSA and PSMA.

In another embodiment of this aspect and all other aspects described herein, the RNA expression levels of PSA and PSMA are determined at the single cell level using an in situ RNA hybridization assay. In another embodiment of this aspect and all other aspects described herein, the RNA expression levels of PSA and PSMA are determined at the single cell level using a qRT-PCR assay.

In another embodiment of this aspect and all other aspects described herein, the expression levels of PSA and PSMA are determined by immunofluorescence staining and/or automated fluorescence microscopy.

Another aspect provided herein relates to a method of determining if a subject is responsive to a prostate cancer treatment comprising assaying isolated circulating tumor cells obtained from a subject being treated for prostate cancer to determine the ratio of prostate specific antigen (PSA) to prostate specific membrane antigen (PSMA) and comparing the ratio to a reference value, wherein if the ratio is reduced compared to the reference value, identifying the individual as being responsive to the prostate cancer treatment.

In one embodiment of this aspect and all other aspects described herein, the reference value comprises a ratio of expression levels determined in the subject or a population of subjects prior to initiation of the treatment for prostate cancer.

In another embodiment of this aspect and all other aspects described herein, the reference value comprises a ratio of expression levels determined in a population determined to have castration-resistant prostate cancer.

In another embodiment of this aspect and all other aspects described herein, the circulating tumor cells are isolated using a microfluidic capture method.

In another embodiment of this aspect and all other aspects described herein, the circulating tumor cells are isolated from a blood sample obtained from the subject.

In another embodiment of this aspect and all other aspects described herein, the expression levels of PSA and PSMA are determined by contacting the isolated circulating tumor cells with antibody reagents specific for PSA and PSMA.

In another embodiment of this aspect and all other aspects described herein, the expression levels of PSA and PSMA are determined by immunofluorescence staining and/or automated fluorescence microscopy.

In another embodiment of this aspect and all other aspects described herein, the RNA expression levels of PSA and PSMA are determined at the single cell level using an in situ RNA hybridization assay. In another embodiment of this aspect and all other aspects described herein, the RNA expression levels of PSA and PSMA are determined at the single cell level using a qRT-PCR assay.

In another embodiment of this aspect and all other aspects described herein, the subject is being treated with bicalutamide, MVD3100, abiraterone acetate, cabazitaxel, sipulecel T, ketoconazole, TAK-700, or a taxane chemotherapeutic agent.

In another embodiment of this aspect and all other aspects described herein, the subject is being treated with a hormone therapy for prostate cancer.

In another embodiment of this aspect and all other aspects described herein, the hormone therapy comprises leuprolide.

Also provided herein, in another aspect, are methods for determining if an individual is responsive to a prostate cancer treatment comprising: (i) isolating circulating tumor cells obtained from a subject determined to have prostate cancer at a first time point and assaying for the ratio of prostate specific antigen (PSA) to prostate specific membrane antigen (PSMA), (ii) administering a prostate cancer agent to the subject, and (iii) isolating circulating tumor cells obtained from a subject determined to have prostate cancer at a second time point and assaying for the ratio of prostate specific antigen (PSA) to prostate specific membrane antigen (PSMA), and (iv) comparing the ratio of PSA/PSMA measured at the second time point to the ratio of PSA/PSMA measured at the first time point, wherein if the ratio at the second time point is decreased compared to the ratio at the first time point, identifying the individual as being responsive to the prostate cancer treatment.

In one embodiment of this aspect and all other aspects described herein, the first time point is prior to initiation of the treatment for prostate cancer.

In another embodiment of this aspect and all other aspects described herein, the first time point is after discontinuation of a hormone therapy.

In another embodiment of this aspect and all other aspects described herein, the circulating tumor cells are isolated using a microfluidic capture method.

In another embodiment of this aspect and all other aspects described herein, the subject is being treated with bicalutamide, MVD3100, abiraterone acetate, cabazitaxel, sipulecel T, ketoconazole, TAK-700, or a taxane chemotherapeutic agent.

In another embodiment of this aspect and all other aspects described herein, the subject is being treated with a hormone therapy for prostate cancer.

In another embodiment of this aspect and all other aspects described herein, the hormone therapy comprises leuprolide.

In another embodiment of this aspect and all other aspects described herein, the circulating tumor cells are isolated from a blood sample obtained from the subject.

In another embodiment of this aspect and all other aspects described herein, the expression levels of PSA and PSMA are determined by contacting the isolated circulating tumor cells with antibody reagents specific for PSA and PSMA.

In another embodiment of this aspect and all other aspects described herein, the expression levels of PSA and PSMA are determined by immunofluorescence staining and/or automated fluorescence microscopy.

In another embodiment of this aspect and all other aspects described herein, the RNA expression levels of PSA and PSMA are determined at the single cell level using an in situ RNA hybridization assay. In another embodiment of this aspect and all other aspects described herein, the RNA expression levels of PSA and PSMA are determined at the single cell level using a qRT-PCR assay.

Also provided herein in another aspect is a method of treating a patient having prostate cancer, the method comprising: (i) isolating circulating tumor cells from a biological sample obtained from a subject, (ii) determining the ratio of prostate specific antigen (PSA) to prostate specific membrane antigen (PSMA) expression, (iii) if the PSA/PSMA expression ratio is increased compared to that of a reference value, administering to the subject a prostate cancer agent that has not been previously administered to the subject.

In one embodiment of this aspect and all other aspects described herein, the prostate cancer agent that has not been previously administered is bicalutamide, MVD3100, abiraterone acetate, cabazitaxel, sipulecel T, ketoconazole, TAK-700, or a taxane chemotherapeutic agent.

In another embodiment of this aspect and all other aspects described herein, the subject having prostate cancer is currently undergoing treatment with a hormone therapy for prostate cancer, or was previously treated with a hormone therapy for prostate cancer.

In another embodiment of this aspect and all other aspects described herein, the hormone therapy comprises leuprolide.

In another embodiment of this aspect and all other aspects described herein, the hormone therapy is discontinued prior to treatment with the prostate cancer agent that has not been previously administered.

In another embodiment of this aspect and all other aspects described herein, the reference value is obtained from a subject or population of subjects having prostate cancer.

In another embodiment of this aspect and all other aspects described herein, the circulating tumor cells are isolated using a microfluidic capture method.

In another embodiment of this aspect and all other aspects described herein, the circulating tumor cells are isolated from a blood sample obtained from the subject.

In another embodiment of this aspect and all other aspects described herein, the expression levels of PSA and PSMA are determined by contacting the isolated circulating tumor cells with antibody reagents specific for PSA and PSMA.

In another embodiment of this aspect and all other aspects described herein, the expression levels of PSA and PSMA are determined by immunofluorescence staining and/or automated fluorescence microscopy.

In another embodiment of this aspect and all other aspects described herein, the RNA expression levels of PSA and PSMA are determined at the single cell level using an in situ RNA hybridization assay. In another embodiment of this aspect and all other aspects described herein, the RNA expression levels of PSA and PSMA are determined at the single cell level using a qRT-PCR assay.

Another aspect provided herein relates to a method of monitoring and guiding prostate cancer therapy in a subject being treated for prostate cancer, the method comprising: (a) determining the ratio of expression levels of prostate specific antigen (PSA) to prostate specific membrane antigen (PSMA) in circulating tumor cells isolated from a biological sample obtained from a subject being treated with a prostate cancer agent, (b) comparing the ratio of expression levels determined in step (a) to a reference value, and if the ratio is increased relative to the reference value, identifying the subject as being non-responsive to the prostate cancer agent.

In one embodiment of this aspect and all other aspects described herein, the hormone therapy comprises leuprolide.

In another embodiment of this aspect and all other aspects described herein, if the ratio is increased treatment with the prostate cancer agent is discontinued and treatment with a prostate cancer agent that has not been previously administered to the subject is initiated.

In another embodiment of this aspect and all other aspects described herein, the prostate cancer agent that has not been previously administered to the subject is bicalutamide, MVD3100, abiraterone acetate, cabazitaxel, sipulecel T, ketoconazole, TAK-700, or a taxane chemotherapeutic agent.

Also provided herein in another aspect is an assay comprising: (a) determining the expression level of prostate specific membrane antigen (PSMA) in circulating tumor cells isolated from a biological sample obtained from a subject determined to have prostate cancer, (b) comparing the expression levels determined in step (a) to a reference value, and if the expression level is decreased relative to the reference value identifying the subject as having a castration-resistant prostate cancer.

In another aspect, provided herein is an assay comprising: (a) determining the expression level of prostate specific membrane antigen (PSMA) in circulating tumor cells isolated from a biological sample obtained from a subject undergoing treatment for prostate cancer, (b) comparing the expression level determined in step (a) to a reference value, wherein if the level determined in step (a) is increased relative to the reference value, identifying the subject as responding to the treatment.

BRIEF DESCRIPTION OF THE FIGURES

(FIG. 1A) Western blot for PSA, PSMA, and alpha-tubulin in LNCaP cells treated with 1 nM R1881 for increasing times after being cultured 3 days in medium containing 10% charcoal-stripped serum (left panel), or treated with 10 µM bicalutamide for increasing times after being cultured under standard conditions (right panel). (FIG. 1B) Pseudocolor density plots of multiparameter immunofluorescence profiles of LNCaP cells treated with 1 nM R1881 after 3 days culture in medium containing 10% charcoal-stripped serum, imaged using an automated fluorescence microscopy scanning system. x- and y-axes represent "area-pixel" single cell signal intensity measurements for PSMA and PSA, respectively. (FIG. 1C) Comparable analysis for LNCaP cells treated with 10 µM bicalutamide after being cultured under standard conditions.

(FIG. 2A) Pseudocolor density plots of multiparameter immunofluorescence profiles of CTCs from patient with castration-sensitive prostate cancer (left panel) and castration-resistant prostate cancer (right panel). X- and y-axes represent "area-pixel" single cell signal intensity measurements for PSMA and PSA, respectively. (FIG. 2B) Box plots demonstrating the relative proportions of AR signaling phenotypes in CTCs from patients with CSPC compared to CRPC prior to initiation of therapy (P=0.015 for % PSA+/PSMA−; P=0.059 for % PSA+/PSMA+; P=0.13 for % PSA−/PSMA+).

(FIG. 3A) Pseudocolor density plots of multiparameter immunofluorescence AR signaling profiles of CTCs in a patient with castration-sensitive prostate cancer before and after ADT with leuprolide showing transformation of CTCs from the "AR-on" (PSA+/PSMA−) phenotype to the "AR-off" (PSA−/PSMA+) phenotype. (FIG. 3B) Box plots showing composite data for relative proportions of AR signaling phenotypes in CTCs from patients with castration-sensitive prostate cancer (n=4) pretreatment and after 4 weeks of ADT (P=0.028 for % PSA+/PSMA−; P=0.41 for % PSA+/PSMA+; P=0.64 for % PSA−/PSMA+).

FIGS. 4A-4D show data relating to AR signaling in CTCs from CRPC patients treated with abiraterone acetate. (FIG. 4A) Pseudocolor density plots of multiparameter immunofluorescence AR signaling profiles of CTCs in a patient with CRPC, showing a decrease in the proportion of PSA+/PSMA− "AR-on" CTCs after initiation of abiraterone acetate. (FIG. 4B) Box plots showing composite data for relative proportions of AR signaling phenotypes in CTCs from patients that exhibit stable or declining proportion of "AR-on" CTCs after initiation of therapy (P=0.17 for % PSA+ only; P=0.14 for % PSA+/PSMA+; P=0.055 for % PSMA+ only). (FIG. 4C) Increase in the proportion of PSA+/PSMA−"AR-on" CTCs observed in a patient with CRPC after treatment with abiraterone acetate. (FIG. 4D) Box plots showing composite data for relative proportions of AR signaling phenotypes in CTCs from patients that exhibit an increasing proportion of "AR-on" CTCs after initiation of therapy (P=0.38 for % PSA+ only; P=0.64 for % PSA+/PSMA+; P=1 for % PSMA+ only).

FIG. 9A depicts images of micromanipulation of single CTCs isolated from a blood specimen of a patient with prostate cancer using the $^{neg}$CTC-iChip and stained in solution with anti-EpCAM and anti-CD45 antibodies. Top panel shows a bright field image merged. Wide arrow represents an EpCAM+/CD45− CTC. Thin arrows points to EpCAM−/CD45+ leukocytes. Arrowhead denotes an erythrocyte. Dashed line outlines the micromanipulator needle tip. Bottom two panels show single channels. Scale bar, 20 μm. FIG. 9B depicts EpCAM and bright field images of 15 single prostate cancer CTCs from a single patient selected for transcriptional profiling. Scale bar, 10 μm. FIG. 9C depicts a table listing the proportional distribution of various gene groups expressed in single CTCs isolated from the prostate cancer patient.

DETAILED DESCRIPTION

Figures 1A, 1B, 1C:
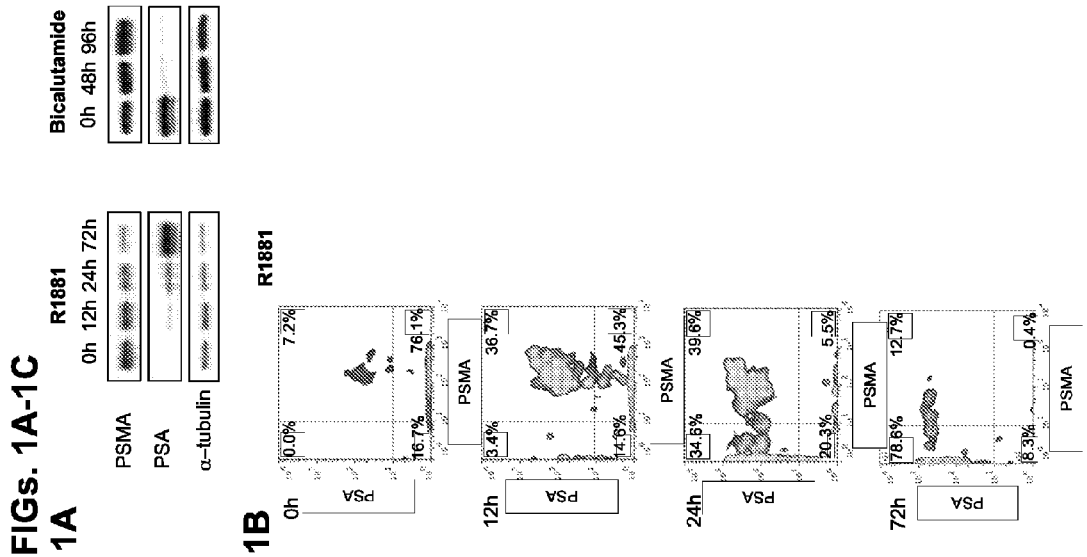
FIGS. 1A-1C show data relating to multiparameter single cell immunofluorescence assay for AR signaling to measure dynamic changes in AR activity in cultured prostate cancer cells.

The methods and assays provided herein are based, in part, on the discovery that ratios of prostate specific antigen (PSA) to prostate specific membrane antigen (PSMA) expression in circulating tumor cells can aid in determining the likelihood that a prostate cancer will or will not respond to a hormonal therapy, and further can be used to monitor therapeutic efficacy of an anti-cancer agent used for the treatment of prostate cancer. Also provided herein are assays and methods related to determining a ratio of expression levels of PSMA in circulating tumor cells for diagnosis and/or monitoring treatment efficacy for prostate cancers that are likely hormone resistant.

Definitions

As used herein, the term "circulating tumor cells" refers to cells that have detached from a primary tumor (e.g., a prostate tumor) and circulate in the bloodstream of a subject having cancer.

As used herein, the term "prostate cancer" refers to a malignant neoplasm of the prostate within a given subject. In one embodiment, the neoplasm is of epithelial origin and is also referred to as a carcinoma of the prostate. For the purposes of the present disclosure, the term "prostate cancer" typically refers to castration-sensitive cancer (e.g., prostate cancer that is responsive to a hormone therapy, as that term is used herein). In one embodiment, the term "prostate cancer" refers to a metastatic prostate cancer. Alternatively, in another embodiment the term "prostate cancer" refers to a localized prostate cancer.

As used herein the term "castration-resistant prostate cancer" refers to a refractory prostate cancer that continues or resumes growth in subjects previously treated or currently undergoing hormone therapy treatment for prostate cancer. Typically, "castration-resistant prostate cancers" are also metastatic prostate cancers. While castration-resistant prostate cancers are no longer responsive to castration treatment (reduction of available androgen/testosterone/DHT by chemical or surgical means), these cancers still show reliance upon hormones for androgen receptor activation. That is, castration-resistant prostate cancers do not respond to hormonal therapies that interfere indirectly with gonadal production of testosterone in the subject (e.g., first-line therapies such as leuprolide, which produces hypogonadism), however they can still respond to anti-androgen therapies that e.g., inhibit specific enzymes in the production of testosterone or downstream activity of the AR itself. For example, some castrate-resistant prostate cancers will respond to abiraterone acetate inhibition of CYP17A1 enzyme inhibition (a second-line hormonal therapy), which reduces production of DHEA and androstenedione (precursors of testosterone). This is in contrast to hormone-therapy resistant prostate cancers that do not respond to any hormonal therapy and are therefore treated using a chemotherapeutic agent that is independent of the AR signaling pathway.

As used herein, the term "hormone therapy" refers to a therapy for the treatment of prostate cancer that deprives a tumor of androgen (e.g., testosterone) or androgen activity in the subject. Such hormone therapies can include e.g., agents that prevent testosterone production, agents that block testosterone action at the level of the cell, or surgical removal of the testes (orchiectomy). In one embodiment, the hormone therapy comprises a gonadotropin-releasing hormone (GnRH) agonist, such as leuprolide (LUPRON™, ELIGARD™), buserelin (SUPREFACT™, SUPRECOR™), goserelin (ZOLADEX™), nafarelin (SYNAREL™), triptorelin (TRELSTAR™), histrelin (SUPPRELIN A™; VANTAS™), deslorelin (SUPRELORIN™; OVUPLANT™), or degarelix (FIRMAGON™). Leuprolide is a common first-line anti-androgen. In another embodiment, the hormone therapy comprises a second-line anti-androgen, such as bicalutamide (CASODEX™; COSUDEX™, CALUTIDE™, KALUMID™), flutamide, or nilutamide (NILANDRON™), among others. In another embodiment, the hormonal therapy comprises abiraterone acetate.

As used herein, an "antibody reagent" encompasses polyclonal and monoclonal antibody preparations, as well as preparations including hybrid or chimeric antibodies, such as humanized antibodies, altered antibodies, F(ab')$_2$ fragments, F(ab) fragments, Fv fragments, single domain antibodies, dimeric and trimeric antibody fragment constructs, minibodies, and functional fragments thereof which exhibit immunological binding properties of the parent antibody molecule and/or which bind a cell surface antigen.

As used herein, the term "biological sample" refers to a fluid sample, a cell sample, a tissue sample, or an organ sample obtained from a subject or patient. For the purposes of isolating circulating tumor cells, the biological sample is typically a whole blood sample, but can also be a partially separated (e.g., centrifuged) blood sample provided that the biological sample comprises at least one circulating tumor cell, as that term is used herein. In some embodiments, while not necessary, a cell or population of cells, an exosome, a quantity of tissue or fluid are obtained from a subject to first detect the presence of prostate cancer prior to isolation of circulating tumor cells. The term "sample" includes any material derived by processing such a sample. Derived samples can, for example, include nucleic acids or proteins extracted from the sample or obtained by subjecting the sample to techniques such as amplification or reverse transcription of mRNA, isolation and/or purification of certain components, etc.

As used herein, the term "reference value" refers to a reference value, or range of values, obtained for PSMA expression or a ratio of PSA/PSMA expression from e.g., at least one subject. In some embodiments, the reference value is obtained from the same subject prior to treatment with an anti-cancer agent for the treatment of prostate cancer or from a population of subjects prior to initiation of such treatment. Alternatively, the reference value or range of values can be obtained from a plurality of subjects in a population substantially free of castration-resistant prostate cancer (e.g., a subject determined to have prostate cancer, wherein the prostate cancer is still responsive to hormonal therapies) or alternatively from a plurality of subjects in a population having castration-resistant or hormonal therapy-resistant prostate cancer. The reference sample can be stored as a value(s) on a computer or PDA device to permit comparison with a value obtained from a subject using the methods described herein. The reference sample can also be obtained from the same subject e.g., at an earlier time point prior to onset of castration resistant prostate cancer or prior to initiation of treatment with an agent for treating prostate cancer using clinical tests known to those of skill in the art. One of skill in the art can determine an appropriate reference sample for use with the methods described herein.

The term "statistically significant" or "significantly" refers to statistical significance and generally means a two standard deviation (2SD) above normal, or higher, e.g., level of PSA/PSMA expression. The term refers to statistical evidence that there is a difference. It is defined as the probability of making a decision to reject the null hypothesis when the null hypothesis is actually true. The decision is often made using the p-value.

As used herein, the term "serially monitoring" when referring to a level of PSA/PSMA in a sample, refers to measuring a ratio of PSA/PSMA expression in a sample of CTCs obtained from a subject on two or more occasions (e.g., doctor's visits). Serial monitoring can be performed on samples obtained from subjects on a quarterly, bimonthly, monthly, biweekly, weekly, every 3 days or on a daily basis. Serial monitoring of a level of PSA/PSMA includes periodically measuring such a ratio at regular intervals as deemed necessary by the skilled artisan.

As used herein, the terms "chemotherapy," "anti-cancer agent," or "chemotherapeutic agent" refer to any chemical agent with therapeutic usefulness in the treatment of diseases characterized by abnormal cell growth, and particularly cell growth associated with prostate cancer. Such diseases include tumors, neoplasms and cancer as well as diseases characterized by hyperplastic growth. An anti-cancer agent or chemotherapeutic agent differs from a hormonal therapy, as the term is used herein, in that an anti-cancer or chemotherapeutic agent does not directly target AR pathways. Typically, in the context of the present disclosure, such chemotherapy agents are considered to be second- or third-line therapies that are applied following failure of a subject to adequately respond to first-line hormonal therapies for treatment of prostate cancer, or more frequently following the emergence of a hormone-resistant phenotype in an individual in which hormonal therapy was initially effective in reducing tumor load. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, and miscellaneous antineoplastic drugs. Most if not all of these agents are directly toxic to cancer cells and do not require immune stimulation. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., ©2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In one embodiment, the chemotherapeutic agent comprises a taxane chemotherapeutic agent. For example, in one embodiment, the chemotherapeutic agent is docetaxol.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a malignant condition or cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but can also include a cessation or at least slowing of progress or worsening of symptoms that would be expected in absence of treatment. Beneficial or desired clinical results include, but are not limited to, alleviation of one or more symptom(s) of a malignant disease, diminishment of extent of a malignant disease, stabilized (i.e., not worsening) state of a malignant disease, delay or slowing of progression of a malignant disease, amelioration or palliation of the malignant disease state, and remission (whether partial or total), whether detectable or undetectable. The term "treatment" of a disease also includes providing relief from the symptoms or side-effects of the disease (including palliative treatment).

As used herein, the term "therapeutically effective amount" means that amount necessary, at least partly, to attain the desired effect, or to delay the onset of, inhibit the progression of, or halt altogether, the onset or progression of the particular disease or disorder being treated (e.g., castration-resistant prostate cancer). Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. In some embodiments, a maximum dose of the anti-cancer agent is used, that is, the highest safe dose according to sound medical judgment. It will be understood by those of ordinary skill in the art, however, that a lower dose or tolerable dose can be administered for medical reasons, psychological reasons or for virtually any other reason.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference value or reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference sample), or any decrease between 10-100% as compared to a reference level.

The terms "increased", "increase" or "enhance" or "activate" are all used herein to generally mean an increase by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein the term "comprising" or "comprises" is used in reference to compositions, methods, and respective component(s) thereof, that are essential to the claimed invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the claimed invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Isolation of Circulating Tumor Cells (CTCs)

Epithelial cells that are released from solid tumors have been found in very low concentrations in the circulation of patients with advanced cancers of the breast, colon, liver, ovary, prostate, and lung. The presence or relative number of these cells in blood has been correlated with overall prognosis and responsiveness of a subject to therapy. These CTCs can aid in the detection of tumor expansion or metastasis before the appearance of clinical symptoms.

CTCs typically have a short half-life (e.g., approximately one day) and their presence generally indicates a recent influx from a proliferating tumor. Therefore, CTCs are part of a dynamic process that can reflect the current clinical status of patient disease and therapeutic response.

CTCs can be isolated from a biological sample, such as a whole blood sample, using any method known to those of skill in the art, provided that the method of isolation will not interfere with determining the expression of PSA or PSMA in the circulating tumor cells. For example, one would not use an antibody against either PSA or PSMA to capture a population of circulating tumor cells from a biological sample, as such methods of CTC capture would interfere with measuring expression of either PSA or PSMA or a ratio thereof.

In one embodiment, the circulating tumor cells are isolated using a microfluidic capture method, such as the method described by Stott et al. *Proc Natl Acad Sci USA* (2010) 107:18392-7, which is incorporated herein by reference in its entirety.

Antibody Reagents for Measuring PSA and/or PSMA Levels

As used herein, the term "antibody reagent" refers to a protein that includes at least one immunoglobulin variable domain or immunoglobulin variable domain sequence and which specifically binds a given antigen. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')$_2$, Fd fragments, Fv fragments, scFv, and domain antibodies (dAb) fragments (de Wildt et al., Eur J. Immunol. 1996; 26(3):629-39)) as well as complete antibodies. An antibody can have the structural features of IgA, IgG, IgE, IgD, IgM (as well as subtypes thereof). Antibodies can be from any source, including primate (human and non-human primate) and primatized antibodies.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; Kabat definitions are used herein). Each VH and VL is typically composed of three CDRs and four FRs, arranged from amino-terminus to carboxy-terminus in the following order: FR1, CDR1, FR2, CDR2, FR3, CDR3, FR4.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. One or more of the framework regions can be human, e.g., FR1, FR2, FR3, and FR4 of the HC or LC. For example, at least 70, 75, 80, 85, 90, 91, 92, 93, 94, 95, 96, 97, 98, 99, or 100% of an immunoglobulin variable domain, the constant region, the constant domains (CH1, CH2, CH3, CL1), or the entire antibody can be human or effectively human. Fully human monoclonal antibodies also can be prepared by immunizing mice transgenic for large portions of human immunoglobulin heavy and light chain loci. Following immunization of these mice (e.g., XENOMOUSE™ (Abgenix), HUMAB-MOUSE™ (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

The term "antigen-binding fragment" is used herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')$_2$ fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883.

Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

Antibody reagents to be used for protein analysis are widely available through commercial sources including AbCam (Cambridge, Mass.), New England Biolabs (Ipswich, Mass.), Santa Cruz Biotechnologies (Santa Cruz, Calif.), and Cell Signaling (Danvers, Mass.), among others.

Antibodies and antibody reagents can also be raised against a polypeptide or portion of a polypeptide by methods known to those skilled in the art. Antibodies are readily raised in animals such as rabbits or mice by immunization with the gene product, or a fragment thereof (e.g., PSA or PSMA). Immunized mice are particularly useful for providing sources of B cells for the manufacture of hybridomas, which in turn are cultured to produce large quantities of monoclonal antibodies. While both polyclonal and monoclonal antibodies can be used in the methods described herein, it is preferred that a monoclonal antibody is used where conditions require increased specificity for a particular protein.

Phage display can also be particularly effective in identifying antibody reagents useful for the methods and assays described herein. Briefly, one prepares a phage library (using e.g., m13, fd, or lambda phage), displaying inserts from 4 to about 80 amino acid residues using conventional procedures. The inserts can represent, for example, a completely degenerate or biased array. One can then select phage-bearing inserts which bind to PSA or PSMA molecules. This process can be repeated through several cycles of reselection of phage that bind to the PSA or PSMA molecules. Repeated rounds lead to enrichment of phage bearing particular sequences. DNA sequence analysis can be conducted to identify the sequences of the expressed polypeptides. The minimal linear portion of the sequence that binds to the PSA or PSMA molecules can be determined. One can repeat the procedure using a biased library containing inserts containing part, or all, of the minimal linear portion plus one or more additional degenerate residues upstream or downstream thereof. Yeast two-hybrid screening methods also may be used to identify polypeptides that bind to the PSA or PSMA molecules. Thus, PSA or PSMA molecules can be used to screen peptide libraries, including phage display libraries, to identify and select peptide binding partners of the PSA or PSMA molecules.

As detailed herein, the foregoing antibody reagents can be used to detect PSA and/or PSMA expression in circulating tumor cells. The antibodies can be coupled to specific diagnostic labeling agents for imaging of the protein or fragment thereof. Labels include, for example, fluorescent or chromogenic labels, as well as antibody fusion proteins, such as antibody-GFP fusions or antibody fusions to other fluorescent proteins known in the art (e.g., enhanced green fluorescent protein (EGFP), Renilla reniformis green fluorescent protein, GFPmut2, GFPuv4, enhanced yellow fluorescent protein (EYFP), enhanced cyan fluorescent protein (ECFP), enhanced blue fluorescent protein (EBFP), citrine and red fluorescent protein from discosoma (dsRED)). A wide variety of fluorescent labels are available from and/or extensively described in the Handbook of Fluorescent Probes and Research Products 8.sup.th Ed. (2001), available from Molecular Probes, Eugene, Oreg., as well as many other manufacturers.

In other embodiments, the antibody reagent is fused to a molecule that is readily detectable either by its presence or activity including, but not limited to, luciferase, chloramphenicol acetyl transferase, β-galactosidase, secreted placental alkaline phosphatase, β-lactamase, human growth hormone, and other secreted enzyme reporters.

PSA and/or PSMA protein from a biological sample comprising at least one circulating tumor cell to be analyzed can be detected or isolated using techniques which are well known to one of skill in the art, including but not limited to immunohistochemistry, Western blot analysis, (i.e.), immunoblotting, ELISA, immunoprecipitation, lateral flow immunoassay, radioimmunoassay, etc.

While it is not necessary to normalize the expression ratio of PSA/PSMA to expression of a housekeeping protein or gene since the use of a ratio is effectively "self-normalizing," one of skill in the art might choose such an approach to reduce variability among samples or among different subjects. Thus, the difference between the expression levels of PSA/PSMA or PSMA alone in circulating tumor cells can be normalized to the expression level of control proteins or nucleic acids, e.g. housekeeping genes whose expression levels are known to be relatively invariant. Exemplary control genes include, but are not limited to, β-actin, and glyceraldehyde 3-phosphate dehydrogenase (GAPDH).

Determining Expression of PSA/PSMA or PSMA

The methods and assays provided herein relate to diagnosing prostate cancer status (e.g., likelihood to respond to hormonal therapies), monitoring prostate cancer progression or monitoring treatment efficacy in a subject. The term "determining the ratio of expression levels of PSA/PSMA" can refer to the determination of the presence or amount of PSA/PSMA expression products, e.g. mRNA transcript(s), and/or the determination of the presence and/or amount of PSA/PSMA protein(s). The determination of the presence or amount of such expression products can be accomplished by any means known in the art.

In one embodiment, measurement of the nucleic acid level of PSA/PSMA expression can be assessed by separation of nucleic acid molecules (e.g. RNA or cDNA) obtained from the circulating tumor cells in agarose or polyacrylamide gels, followed by hybridization with PSA– or PSMA–specific oligonucleotide probes. This approach requires a considerable amount of cellular material. Alternatively, the expression level can be determined by the labeling of nucleic acid obtained from the sample followed by separation on a sequencing gel. Comparison of expression levels can be accomplished visually or by means of a densitometer. Methods for the detection of mRNA or expression products are known to the person skilled in the art.

Alternatively, nucleic acid levels of PSA/PSMA expression can be detected using a DNA array or microarray approach. Typically, sample nucleic acids derived from subjects to be tested are processed and labeled, preferably with a fluorescent label. Subsequently, such nucleic acid molecules can be used in a hybridization approach with immobilized capture probes corresponding to the PSA- or PSMA molecule. Suitable means for carrying out microarray analyses are known to the person skilled in the art.

In another embodiment, the nucleic acid level of PSA/PSMA or PSMA expression is detected using quantitative RT-PCR, including e.g., real-time PCR following reverse transcription of PSA- and PSMA mRNA transcripts. In some embodiments, Taqman, Molecular Beacon probes or other FRET-based probes can be used for quantitative PCR detection. Methods relating to the use of such probes are well known to those of skill in the art.

In another embodiment, in situ RNA hybridization (RNAish) assays are used to quantitatively measure RNA transcripts at the single molecule level in single cells. In one embodiment, a QUANTIGENE VIEWRNA™ assay (AFFYMETRIX™, Santa Clara, Calif.) is used to measure gene expression levels of PSA/PSMA or PSMA alone.

Determination of protein expression levels of PSA and PSMA or of any fragments, homologues or derivatives thereof can be carried out using any suitable detection technique known in the art. In some embodiments, the protein levels of PSA and PSMA are determined immunologically, e.g. by using antibody reagents specific for the PSA and PSMA proteins.

Determination of the protein levels of the PSA/PSMA protein can be accomplished, for example, by the use of antibody reagents as described herein in a Western blot analysis. Alternatively, proteins can be separated by two-dimensional gel electrophoresis systems. Two-dimensional gel electrophoresis is well known in the art and typically involves iso-electric focusing along a first dimension followed by SDS-PAGE electrophoresis along a second dimension. These methods also require a considerable amount of cellular material. The analysis of 2D SDS-PAGE gels can be performed by determining the intensity of protein spots on the gel, or can be performed using immune detection. In other embodiments, protein samples are analyzed by mass spectroscopy.

Immunological tests can be used with the methods and assays described herein and include, for example, competitive and non-competitive assay systems using techniques such as Western blots, radioimmunoassay like RIA (radio-linked immunoassay), ELISA (enzyme linked immunosorbent assay), "sandwich" immunoassays, immunoprecipitation assays, immunodiffusion assays, agglutination assays, e.g. latex agglutination, complement-fixation assays, immunoradiometric assays, fluorescent immunoassays, e.g. FIA (fluorescence-linked immunoassay), chemiluminescence immunoassays, electrochemiluminescence immunoassay (ECLIA) and protein A immunoassays. Such assays are routine and well known to those of skill in the art.

Where circulating tumor cells tend to be relatively rare, methods suited to the measurement of PSA/PSMA and their ratio in single cells are of particular interest. Microfluidic capture as described herein above, and in the Examples section permits enrichment for CTCs and fluorescent microscopic analyses of individual cells stained for PSA and PSMA with labeled antibody reagents.

Reference Values

The terms "reference value," "reference level," "reference sample," and "reference" are used interchangeably herein and refer to the level of PSMA expression or PSA/PSMA expression in a known sample against which another sample (i.e., one obtained from a subject having a cancer suspected to be castration-resistant or hormone therapy resistant) is compared. A reference value is useful for determining the amount of PSMA expression or ratio of PSA/PSMA expression or the relative increase/decrease of such expressional levels/ratios in a biological sample. A reference value serves as a reference level for comparison, such that samples can be normalized to an appropriate standard in order to infer the presence, absence or extent of castrate-resistance or hormone therapy-resistance of a prostate cancer in a subject.

In one embodiment, a biological standard is obtained at an earlier time point (e.g., prior to the onset of a prostate cancer that does not respond to hormonal therapies) from the same individual that is to be tested or treated as described herein. Alternatively, a standard can be from the same individual having been taken at a time after the onset or diagnosis of a hormone-resistant cancer. In such instances, the reference value can provide a measure of the efficacy of treatment. It can be useful to use as a reference for a given patient a level or ratio from a sample taken after prostate cancer diagnosis but before the administration of any therapy to that patient.

Alternatively, a reference value can be obtained, for example, from a known biological sample from a different individual (e.g., not the individual being tested) that is e.g., substantially free of hormone therapy-resistant or castration-resistant prostate cancer or that is known to be a non-responder to hormone therapy treatment for e.g., castration-resistant prostate cancer. A known sample can also be obtained by pooling samples from a plurality of individuals to produce a reference value or range of values over an averaged population, wherein a reference value represents an average level of PSMA or an average ratio of PSA/PSMA among a population of individuals (e.g., a population of individuals having hormone-resistant prostate cancer or a population of individuals having a hormone-sensitive prostate cancer). Thus, the level of PSMA or PSA/PSMA in a reference value obtained in this manner is representative of an average level of this marker in a general population of individuals having prostate cancer, or a population of individuals having a hormone therapy-resistant prostate cancer. An individual sample is compared to this population reference value by comparing expression of PSMA or PSA/PSMA from a sample relative to the population reference value. Generally, a decrease in the amount of PSMA or an increase in the ratio of PSA/PSMA over the reference value (e.g., a reference obtained from subjects having prostate cancer) indicates or predicts the presence of hormone therapy resistance, while an increase in the amount of PSMA or a decrease in the ratio of PSA/PSMA indicates or predicts that the cancer is less likely to be resistant to hormonal therapies. The converse is contemplated in cases where a reference value is obtained from a population of subjects having hormone-resistant prostate cancer. It should be noted that there is often variability among individuals in a population, such that some individuals will have higher levels of PSMA or PSA/PSMA expression, while other individuals have lower levels of expression. However, one skilled in the art can make logical inferences on an individual basis regarding the detection and treatment of cancer as described herein.

In one embodiment, a range of values for PSA/PSMA or PSMA in circulating tumor cells can be defined for a plurality of hormone-sensitive individuals and for a plurality of hormone-resistant individuals having prostate cancer. Provided that the number of individuals in each group is sufficient, one can define a range of PSA/PSMA values for each population. These values can be used to define cut-off points for selecting a therapy or for monitoring progression of disease. Thus, one of skill in the art can determine a ratio of PSA/PSMA and compare the value to the ranges in each particular sub-population to aid in determining the status of disease and the recommended course of treatment. Such value ranges are analogous to e.g., HDL and LDL cholesterol levels detected clinically. For example, LDL levels below 100 mg/dL are considered optimal and do not require therapeutic intervention, while LDL levels above 190 mg/dL are considered 'very high' and will likely require some intervention. One of skill in the art can readily define similar parameters for PSA/PSMA ratios in hormone-sensitive and hormone-resistant prostate cancers. These value ranges can be provided to clinicians, for example, on a chart, programmed into a PDA etc.

A standard comprising a reference value or range of values can also be synthesized. A known amount of PSMA or PSA/PSMA (or a series of known amounts) can be prepared within the typical expression range for PSMA or PSA/PSMA that is observed in a general prostate cancer population. This method has an advantage of being able to compare the extent of disease in one or more individuals in a mixed population. This method can also be useful for subjects who lack a prior sample to act as a reference value or for routine follow-up post-diagnosis. This type of method can also allow standardized tests to be performed among several clinics, institutions, or countries etc.

Pharmaceutically Acceptable Carriers

Therapeutic compositions of the agents disclosed herein contain a physiologically tolerable carrier together with an active agent as described herein, dissolved or dispersed therein as an active ingredient. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without toxicity or the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein.

Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Therapeutic compositions used herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

Prostate Cancer and Treatment Thereof

Prostate cancer can be treated using a variety of approaches. Typically, prostate cancer when first diagnosed is responsive to testosterone, and the growth of the prostate cancer can be slowed or inhibited by using testosterone inhibitors or by otherwise reducing the available testosterone. For slow growing prostate cancer in older males, often no therapy is recommended because other causes of mortality are more likely to dominate in this population and the side-effects of therapy can adversely impact the quality of life in this subset of patients. Typically, in younger males at this stage of disease, hormone therapy is used for treatment of prostate cancer and promotes remission in many patients.

Unfortunately, after remission prostate cancer often returns in a form non-responsive to withdrawal of testosterone, i.e., castration-resistant prostate cancer that is almost always terminal. Such hormone resistant prostate cancers can be treated with surgical intervention; however, not all prostate cancers are suitable for surgery. When required, treatment can also include local radiation, and/or complete or partial removal of the prostate and/or even orchieoctomy (castration to reduce testosterone levels). Aggressive prostate cancers that are resistant to surgical intervention can be treated with chemotherapy. Such chemotherapeutic agents include adriamycin, docetaxel, estramustine, mitoxantrone, paclitaxel, other taxanes, prednisone, and immunotherapy targeting various antigens, such as using Sipuleucel, vaccines and nilutamide, among others and can be administered alone or in a combination.

Application of the Methods and Assays Described Herein to Direct Treatment

In general, when a subject is first diagnosed with prostate cancer, they are treated with a standard hormonal therapy (e.g., leuprolide) to which essentially everyone initially responds. However, the recurrence of prostate cancer in spite of treatment with e.g., leuprolide occurs in most patients within a few years. In one embodiment, the detection of increasing values of PSA/PSMA expression ratios over time during treatment with a first-line therapy can permit one to detect signs of resistance to the first-line therapy earlier than the detection of e.g., tumor size, metastases, or clinical development of secondary cancers resulting from resistance of the prostate cancer to the therapy.

In addition, one can use the methods and assays described herein to direct treatment of a prostate cancer that becomes resistant to a first-line hormonal therapy. In an exemplary embodiment, a subject having prostate cancer develops resistance to a first-line hormonal therapy, such as leuprolide. At this stage, a new therapy will need to be selected for treatment of the prostate cancer. Thus, one can determine the expression ratio of PSA/PSMA prior to initiation of a second-line therapy (e.g., abiraterone acetate or a chemotherapeutic agent) and serially monitor the PSA/PSMA expression ratios during treatment with the second-line therapy over time. If the PSA/PSMA ratio levels decrease during or following treatment, then the treatment is considered to be effective. In such cases, the treatment is continued, and/or the dose/regimen etc. is simply adjusted. However, if the PSA/PSMA ratio remains the same or increases during the period of treatment with a second-line therapy, one can discontinue that particular treatment and initiate a treatment regimen with a different agent that has not been previously administered to the subject. While the present clinical guidelines are unclear as to whether one of skill in the art should first treat with a second-line hormonal agent such as abiraterone acetate or a chemotherapeutic agent, the methods and assays described herein can readily assess an efficacious treatment. Alternatively, the methods and assays described herein can efficiently identify a non-efficacious treatment, permitting one to select a new therapy for the subject rapidly.

Chemotherapeutic Agents

In some embodiments, the methods for treating a prostate cancer can further include the use of one or more additional anti-cancer or chemotherapeutic agents. In some embodiments, the anti-cancer agent comprises an agent from the taxane family including, but not limited to, paclitaxel (Taxol™), docetaxel (Taxotere™), cabazitaxel (Jevtana™; XRP-6258), and analogs thereof (i.e., XRP9881; see Ojima and Geney, Curr Opin Investig Drugs 4:73 7, 2004). Members of this class of molecules are β-tubulin binders and stabilize microtubules in a polymerized form. In one embodiment, the anti-cancer agent comprises docetaxol. In another embodiment, the anti-cancer agent comprises cabazitaxel.

Non-limiting examples of chemotherapeutic agents can include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; chloranbucil; GEMZAR® gemcitabine; 6-thioguanine; mercaptopurine; platinum analogs such as cisplatin, oxaliplatin and carboplatin; vinblastine; platinum; etoposide (VP-16); ifosfamide; mitoxantrone; vincristine; NAVELBINE®. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Dosage and Administration

In one aspect, the methods described herein provide a method for treating prostate cancer in a subject. In one embodiment, the subject can be a mammal. In another embodiment, the mammal can be a human, although the approach is effective with respect to all mammals. In one embodiment, the method comprises administering to the subject an effective amount of a pharmaceutical composition comprising an agent that results in an increase in PSMA expression or a decrease in PSA/PSMA ratio, in a pharmaceutically acceptable carrier.

The dosage range for the agent depends upon the potency, and includes amounts large enough to produce the desired effect, e.g., an increase in PSMA expression or a decrease in PSA/PSMA ratio. The dosage should not be so large as to cause unacceptable adverse side effects. Generally, the dosage will vary with the type of agent or inhibitor (e.g., an antibody or fragment, small molecule, siRNA, etc.), and with the age, condition, and sex of the patient. The dosage can be determined by one of skill in the art and can also be adjusted by the individual physician in the event of any complication. Typically, the dosage will range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

Administration of the doses recited above can be repeated for a limited period of time or as necessary. In some embodiments, the doses are given once a day, or multiple times a day, for example but not limited to three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in e.g., PSMA or PSA/PSMA ratio, tumor size, tumor volume, tumor growth rate, etc. (see "Efficacy Measurement" below). Such effective amounts can be gauged in clinical trials as well as animal studies for a given inhibitor.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. For the treatment of tumors, the agent can be administered systemically, or alternatively, can be administered directly to the tumor e.g., by intratumor injection or by injection into the tumor's primary blood supply.

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

An agent can be targeted by means of a targeting moiety, such as e.g., an antibody or targeted liposome technology. In some embodiments, an agent or inhibitor can be targeted to tissue- or tumor-specific targets by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors to cell surface molecules. The addition of an antibody to an agent or inhibitor permits the agent attached to accumulate additively at the desired target site. Antibody-based or non-antibody-based targeting moieties can be employed to deliver a ligand or the inhibitor to a target site. Preferably, a natural binding agent for an unregulated or disease associated antigen is used for this purpose.

Efficacy Measurement

The efficacy of a given treatment for a prostate cancer can be determined by the skilled clinician. However, a treatment is considered "effective treatment," as the term is used herein, if any one or all of the signs or symptoms of, as but one example, cancer are altered in a beneficial manner, other clinically accepted symptoms or markers of disease are improved or ameliorated, e.g., by at least 10% following treatment with an inhibitor. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the pathogenic growth of cancer cells; or (2) relieving the disease, e.g., causing regression of symptoms, reducing the size of a tumor; and (3) preventing or reducing the likelihood of the development of a castration-resistant cancer or a metastatic disease thereof.

An effective amount for the treatment of cancer (e.g., a prostate cancer) means that amount which, when administered to a mammal in need thereof, is sufficient to result in effective treatment as that term is defined herein, for that disease. Efficacy of an agent can be determined by assessing physical indicators of cancer, such as e.g., tumor size, tumor volume, tumor growth rate, metastatic phenotype, etc.

In one embodiment, efficacy of a treatment can be determined by measuring a decrease in PSA/PSMA ratios, as described herein. In another embodiment, efficacy of a treatment can be determined by the re-emergence of sensitivity to a hormone therapy for prostate cancer (e.g., leuprolide sensitivity).

Monitoring Prostate Cancer

In some embodiments, the methods and assays disclosed herein are used to monitor progression of prostate cancer from a cancer that responds to hormone therapy to a prostate cancer that does not respond to a hormone therapy. Further, the methods and assays disclosed herein can be used to monitor the reverse progression (e.g., progression from a hormone non-responsive prostate cancer to a more responsive prostate cancer) upon treatment with a prostate cancer therapy. Monitoring can occur e.g. during a treatment procedure or during a certain period of time, typically during 2 months, 3 months, 4 months, 6 months, 1 year, 2 years, 3 years, 5 years, 10 years, or any other period of time. One of skill in the art can compare the ratio of expression of PSA/PSMA in circulating tumor cells compared to a reference value in any type of periodic time segment, e.g. every week, every 2 weeks, every month, every 2, 3, 4, 5, 6, 7, 8, 9, 10, 11 or 12 months, every 1.5 year, every 2, 3, 4, 5, 6, 7, 8, 9 or 10 years, during any period of time, e.g., during 2 weeks, 3 weeks, 1, 2, 3, 4, 5, 6, 7, 8, 9, 10, 11, 12 months, 1.5, 2, 3, 4, 5, 6, 7, 8, 9, 10, 15 or 20 years, respectively. In some embodiments, the treatment scheme being monitored can be adjusted, e.g. enforced or attenuated, or altered in any suitable manner in correspondence with the results of the monitoring process.

The term "progression of prostate cancer" as used herein relates to a switch between different stages of prostate cancer development, e.g. stages 0 and I to IV of the TNM classification, or any other stage or sub-stage, starting from a healthy condition up to a terminal cancer scenario. Typically, progression towards hormone-resistant prostate cancers is accompanied by an increase in the ratio of expression of PSA/PSMA in a test sample in comparison to a previous test sample from the same individual, e.g. in comparison to a sample derived from a hormone-dependent prostate tumor or tumor control or a hormone-sensitive prostate tumor or tumor control.

Systems

Embodiments of the technology described herein also provide for systems (and computer readable media for causing computer systems) to perform a method for diagnosing a castration-resistant prostate cancer in a subject, assessing a subject's risk of developing a castration-resistant prostate cancer, or monitoring efficacy of a treatment administered for a castration-resistant prostate cancer.

Embodiments of the technology can be described through functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times. Furthermore, it should be appreciated that the modules may perform other functions, thus the modules are not limited to having any particular functions or set of functions.

The computer readable storage media #30 can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (eraseable programmable read only memory), EEPROM (electrically eraseable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing. Computer-readable storage media do not encompass a signal.

Computer-readable data embodied on one or more computer-readable storage media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable storage media on which such instructions are embodied may reside on one or more of the components of either of a system, or a computer readable storage medium as described herein, can be distributed across one or more of such components.

The computer-readable storage media can be transportable such that the instructions stored thereon can be loaded onto any computer resource to implement the aspects of the present invention discussed herein. In addition, it should be appreciated that the instructions stored on the computer-readable medium, described above, are not limited to instructions embodied as part of an application program running on a host computer. Rather, the instructions can be embodied as any type of computer code (e.g., software or microcode) that can be employed to program a computer to implement aspects of the present invention. The computer executable instructions can be written in a suitable computer language or combination of several languages. Basic computational biology methods are known to those of ordinary skill in the art and are described in, for example, Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

The functional modules of certain embodiments of the invention include at minimum a determination system #40, a storage device #30, a comparison module #80, and a display module #110. The functional modules can be executed on one, or multiple, computers, or by using one, or multiple, computer networks. The determination system has computer executable instructions to provide e.g., expression information in computer readable form.

The determination system #40, can comprise any system for detecting a signal representing the expression of PSA or PSMA. Such systems can include microscope data acquisition systems, including single cell fluorescence microscope data acquisition systems, RNA expression arrays, RT-PCR etc.

The information determined in the determination system can be read by the storage device #30. As used herein the "storage device" is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media. The storage device is adapted or configured for having recorded thereon values representing information relating to the expression level of PSA/PSMA or PSMA. Such information can be provided in digital form that can be transmitted and read electronically, e.g., via the Internet, on diskette, via USB (universal serial bus) or via any other suitable mode of communication.

As used herein, "stored" refers to a process for encoding information on the storage device. Those skilled in the art can readily adopt any of the presently known methods for recording information on known media to generate manufactures comprising expression information.

In one embodiment the reference data stored in the storage device to be read by the comparison module is e.g., expression data obtained from a population of subjects that do not have a castration-resistant prostate cancer.

The "comparison module" #80 can use a variety of available software programs and formats for the comparison operative to compare sequence information data determined in the determination system to reference samples and/or stored reference data. In one embodiment, the comparison module is configured to use pattern recognition techniques to compare information from one or more entries to one or more reference data patterns. The comparison module can be configured using existing commercially-available or freely-available software for comparing patterns, and may be optimized for particular data comparisons that are conducted. The comparison module provides computer readable information related to the expression of PSMA or PSA/PSMA in a subject.

The comparison module, or any other module of the invention, can include an operating system (e.g., UNIX) on which runs a relational database management system, a World Wide Web application, and a World Wide Web server. World Wide Web application includes the executable code necessary for generation of database language statements (e.g., Structured Query Language (SQL) statements). Generally, the executables will include embedded SQL statements. In addition, the World Wide Web application may include a configuration file which contains pointers and addresses to the various software entities that comprise the server as well as the various external and internal databases which must be accessed to service user requests. The configuration file also directs requests for server resources to the appropriate hardware—as may be necessary should the server be distributed over two or more separate computers. In one embodiment, the World Wide Web server supports a TCP/IP protocol. Local networks such as this are sometimes referred to as "Intranets." An advantage of such Intranets is that they allow easy communication with public domain databases residing on the World Wide Web (e.g., the GenBank or Swiss Pro World Wide Web site). Thus, in a particular preferred embodiment of the present invention, users can directly access data (via Hypertext links for example) residing on Internet databases using a HTML interface provided by Web browsers and Web servers.

The comparison module provides a computer readable comparison result that can be processed in computer readable form by predefined criteria, or criteria defined by a user, to provide a content based in part on the comparison result that can be stored and output as requested by a user using a display module #110.

The content based on the comparison result, can be an increased expression ratio of PSA/PSMA or a decreased level of PSMA compared to a reference indicating the presence of a castration resistant prostate cancer in a subject. Alternatively, the content based on the comparison result can be the decrease of PSA/PSMA ratio or an increased expression of PSMA compared to a reference indicating that the subject is responsive to the administered treatment.

In one embodiment of the invention, the content based on the comparison result is displayed on a computer monitor #120. In one embodiment of the invention, the content based on the comparison result is displayed through printable media #130, #140. The display module can be any suitable device configured to receive from a computer and display computer readable information to a user. Non-limiting examples include, for example, general-purpose computers such as those based on Intel PENTIUM-type processor, Motorola PowerPC, Sun UltraSPARC, Hewlett-Packard PA-RISC processors, any of a variety of processors available from Advanced Micro Devices (AMD) of Sunnyvale, Calif., or any other type of processor, visual display devices such as flat panel displays, cathode ray tubes and the like, as well as computer printers of various types.

In one embodiment, a World Wide Web browser is used for providing a user interface for display of the content based on the comparison result. It should be understood that other modules of the invention can be adapted to have a web browser interface. Through the Web browser, a user may construct requests for retrieving data from the comparison module. Thus, the user will typically point and click to user interface elements such as buttons, pull down menus, scroll bars and the like conventionally employed in graphical user interfaces.

The methods described herein therefore provide for systems (and computer readable media for causing computer systems) to perform methods for diagnosing castration-resistant prostate cancers or assessing efficacy of a treatment for such cancers in a subject.

Systems and computer readable media described herein are merely illustrative embodiments of the invention for performing methods of diagnosis in an individual, and are not intended to limit the scope of the invention. Variations of the systems and computer readable media described herein are possible and are intended to fall within the scope of the invention.

The modules of the machine, or those used in the computer readable medium, can assume numerous configurations. For example, function may be provided on a single machine or distributed over multiple machines.

Kits

A kit is any manufacture (e.g., a package or container) comprising at least one reagent, e.g., an antibody reagent(s), for specifically detecting a marker of prostate cancer (e.g., PSMA and/or PSA), the manufacture being promoted, distributed, or sold as a unit for performing the methods or assays described herein. When the kits, and methods described herein are used for diagnosis and/or treatment of a prostate cancer, the PSMA or PSA detection probes or systems can be selected such that a positive result is obtained in at least about 20%, at least about 40%, at least about 60%, at least about 80%, at least about 90%, at least about 95%, at least about 99% or in 100% of subjects afflicted with a hormone therapy-resistant prostate cancer.

When the expression level of PSA/PSMA or PSMA is used in the methods and assays described herein, the expression level and/or activity of PSA/PSMA or PSMA can be compared with the expression level of the marker in non-cancerous samples of the same type or to another reference value or reference standard as described herein.

The kits described herein include reagents and/or components that permit assaying circulating tumor cells in a sample (e.g., circulating tumor cells isolated from a sample obtained from a subject). The kits described herein comprise components useful for assessing the presence of a hormone therapy-resistant prostate cancer (e.g., in a sample such as a subject sample). The kit can comprise one or more reagents capable of detecting the expression level of PSMA or PSA e.g., antibody reagents specific for PSMA or PSA. Such components or reagents can permit detection of expression levels directly using e.g., detectable labels, or indirectly e.g., Western blotting of PSA/PSMA or PSMA. Suitable reagents for binding PSMA or PSA include polyclonal antibodies, monoclonal antibodies, or fragments thereof. In some embodiments, the antibody reagents are fixed to a substrate.

The kits described herein can optionally comprise additional components useful for performing the methods and assays described herein. By way of example, the kit can comprise fluids (e.g., buffers) suitable for binding an antibody with a protein with which it specifically binds, one or more sample compartments, an instructional material which describes performance of a method as described herein, a sample of normal cells, a sample of cancer cells (e.g., circulating tumor cells), and the like.

In some embodiments, the kits described herein comprise one or more of the following: a probe for detecting PSMA or PSA/PSMA expression, PCR primers for detecting such expression, a primer for reverse transcription of PSMA or PSA RNA to cDNA, a DNA polymerase, a reverse transcriptase, an anti-cancer agent (e.g., abiraterone acetate), an antibody directed against PSMA or PSA, buffers, solutions, etc.

Preferably, a diagnostic kit for use with the methods and assays disclosed herein contains detection reagents for PSA and PSMA proteins. Such detection reagents comprise in addition to antibody reagents specific for PSA and PSMA, for example, buffer solutions, labels or washing liquids etc. Furthermore, the kit can comprise an amount of a known protein, which can be used for a calibration of the kit or as an internal control. Typically, a diagnostic kit for the detection of PSA/PSMA expression products may comprise accessory ingredients like a PCR buffers, dNTPs, a polymerase, ions like bivalent cations or monovalent cations as co-factors, hybridization solutions etc. A diagnostic kit for the detection of PSA/PSMA proteins can also comprise accessory ingredients like secondary affinity ligands, e.g., secondary antibodies, detection dyes and any other suitable compound or liquid necessary for the performance of a protein detection method known to the person skilled in the art. Such ingredients are known to the person skilled in the art and may vary depending on the detection method carried out. Additionally, the kit may comprise an instruction leaflet and/or may provide information as to the relevance of the obtained results.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. An assay comprising: (a) determining the ratio of expression levels of prostate specific antigen (PSA) to prostate specific membrane antigen (PSMA) in circulating tumor cells isolated from a biological sample obtained from a subject determined to have prostate cancer, (b) comparing the ratio of expression levels determined in step (a) to a reference value, and if the ratio is increased relative to the reference value identifying the subject as being unlikely to respond to hormonal therapy, and if the ratio is the same or reduced relative to the reference value identifying the subject as likely to respond to hormonal therapy.

2. The assay of paragraph 1, wherein the biological sample obtained from a subject comprises a blood sample.

3. The assay of paragraph 1, wherein the reference value is obtained from a subject or population of subjects with prostate cancer.

4. The assay of paragraph 1, wherein the reference value is obtained from the same subject at an earlier time point.

5. The assay of paragraph 1, wherein the circulating tumor cells are isolated using a microfluidic capture method.

6. The assay of paragraph 1, wherein the prostate cancer is metastatic prostate cancer.

7. The assay of paragraph 7, wherein the subject was previously being treated with a hormone therapy for prostate cancer, or is currently being treated with a hormone therapy for prostate cancer.

8. The assay of paragraph 1, wherein the hormone therapy for prostate cancer comprises leuprolide.

9. The assay of paragraph 1, wherein the expression levels of PSA and PSMA are determined by contacting the isolated circulating tumor cells with antibody reagents specific for PSA and PSMA.

10. The assay of paragraph 9, wherein the expression levels of PSA and PSMA are determined by immunofluorescence staining and/or automated fluorescence microscopy.

11. An assay comprising: (a) determining the ratio of expression levels of prostate specific antigen (PSA) to prostate specific membrane antigen (PSMA) in circulating tumor cells isolated from a biological sample obtained from a subject undergoing treatment for prostate cancer, (b) comparing the ratio of expression levels determined in step (a) to a reference value, wherein if the ratio determined in step (a) is reduced relative to the reference value, identifying the subject as responding to the treatment.

12. The assay of paragraph 11, wherein the reference value comprises a ratio of expression levels determined in the subject or a population of subjects prior to initiation of the treatment for prostate cancer.

13. The assay of paragraph 11, wherein the reference value comprises a ratio of expression levels determined in a population of subjects determined to have castration-resistant prostate cancer.

14. The assay of paragraph 11, wherein the biological sample obtained from a subject comprises a blood sample.

15. The assay of paragraph 11, wherein the prostate cancer is metastatic prostate cancer.

16. The assay of paragraph 11, wherein the treatment for prostate cancer comprises leuprolide.

17. The assay of paragraph 11, wherein the circulating tumor cells are isolated using a microfluidic capture method.

18. The assay of paragraph 11, wherein the expression levels of PSA and PSMA are determined by contacting the isolated circulating tumor cells with antibody reagents specific for PSA and PSMA.

19. The assay of paragraph 18, wherein the expression levels of PSA and PSMA are determined by immunofluorescence staining and/or automated fluorescence microscopy.

20. The assay of paragraph 11, wherein the subject is being treated with bicalutamide, MVD3100, abiraterone acetate, cabazitaxel, sipulecel T, ketoconazole, TAK-700, or a taxane chemotherapeutic agent.

21. An assay comprising: (a) isolating circulating tumor cells (CTCs) from a blood sample obtained from a subject undergoing treatment for prostate cancer, (b) measuring the level of expression of prostate specific antigen (PSA) and prostate specific membrane antigen (PSMA) in isolated CTCs, (c) determining the ratio of expression of PSA/PSMA, and (d) comparing the ratio of expression of PSA/PSMA to a reference value, wherein if the ratio determined in step (a) is reduced relative to the reference value, identifying the subject as responding to the treatment.

22. The assay of paragraph 21, wherein the reference value comprises a ratio of expression levels determined in the subject or a population of subjects prior to initiation of the treatment for prostate cancer.

23. The assay of paragraph 21, wherein the reference value comprises a ratio of expression levels determined in a population of subjects determined to have castration-resistant prostate cancer.

24. The assay of paragraph 21, wherein the biological sample obtained from a subject comprises a blood sample.

25. The assay of paragraph 21, wherein the circulating tumor cells are isolated using a microfluidic capture method.

26. The assay of paragraph 21, wherein the expression levels of PSA and PSMA are determined by contacting the isolated circulating tumor cells with antibody reagents specific for PSA and PSMA.

27. The assay of paragraph 26, wherein the expression levels of PSA and PSMA are determined by immunofluorescence staining and/or automated fluorescence microscopy.

28. The assay of paragraph 21, wherein the subject is being treated with bicalutamide, MVD3100, abiraterone acetate, cabazitaxel, sipulecel T, ketoconazole, TAK-700, or a taxane chemotherapeutic agent.

29. A method of treating a patient determined to have prostate cancer, the method comprising: administering to a patient determined to have a ratio of prostate specific antigen (PSA) to prostate specific membrane antigen (PSMA) expression in isolated circulating tumor cells that is increased compared to that of a reference value, a pharmaceutically effective amount of a prostate cancer agent that has not been previously administered to the patient.

30. The method of paragraph 29, wherein the prostate cancer agent that has not been previously administered is bicalutamide, MVD3100, abiraterone acetate, cabazitaxel, sipulecel T, ketoconazole, TAK-700, or a taxane chemotherapeutic agent.

31. The method of paragraph 29, wherein the subject is currently undergoing treatment with a hormone therapy for prostate cancer, or was previously treated with a hormone therapy for prostate cancer.

32. The method of paragraph 31, wherein the hormone therapy comprises leuprolide.

33. The method of paragraph 31, wherein the hormone therapy is discontinued prior to treatment with the anti-cancer agent.

34. The method of paragraph 29, wherein the reference value is obtained from a subject or population of subjects having prostate cancer.

35. The method of paragraph 29, wherein the circulating tumor cells are isolated using a microfluidic capture method.

36. The method of paragraph 29, wherein the circulating tumor cells are isolated from a blood sample obtained from the subject.

37. The method of paragraph 29, wherein the expression levels of PSA and PSMA are determined by contacting the isolated circulating tumor cells with antibody reagents specific for PSA and PSMA.

38. The method of paragraph 37, wherein the expression levels of PSA and PSMA are determined by immunofluorescence staining and/or automated fluorescence microscopy.

39. A method of determining if a subject is responsive to a prostate cancer treatment comprising assaying isolated circulating tumor cells obtained from a subject being treated for prostate cancer to determine the ratio of prostate specific antigen (PSA) to prostate specific membrane antigen (PSMA) and comparing the ratio to a reference value, wherein if the ratio is reduced compared to the reference value, identifying the individual as being responsive to the prostate cancer treatment.

40. The method of paragraph 39, wherein the reference value comprises a ratio of expression levels determined in the subject or a population of subjects prior to initiation of the treatment for prostate cancer.

41. The method of paragraph 39, wherein the reference value comprises a ratio of expression levels determined in a population determined to have castration-resistant prostate cancer.

42. The method of paragraph 39, wherein the circulating tumor cells are isolated using a microfluidic capture method.

43. The method of paragraph 39, wherein the circulating tumor cells are isolated from a blood sample obtained from the subject.

44. The method of paragraph 39, wherein the expression levels of PSA and PSMA are determined by contacting the isolated circulating tumor cells with antibody reagents specific for PSA and PSMA.

The method of paragraph 44, wherein the expression levels of PSA and PSMA are determined by immunofluorescence staining and/or automated fluorescence microscopy.

46. The method of paragraph 39, wherein the subject is being treated with bicalutamide, MVD3100, abiraterone acetate, cabazitaxel, sipulecel T, ketoconazole, TAK-700, or a taxane chemotherapeutic agent.

47. The method of paragraph 39, wherein the subject is being treated with a hormone therapy for prostate cancer.

48. The method of paragraph 47, wherein the hormone therapy comprises leuprolide.

49. A method of determining if an individual is responsive to a prostate cancer treatment comprising: (i) isolating circulating tumor cells obtained from a subject determined to have prostate cancer at a first time point and assaying for the ratio of prostate specific antigen (PSA) to prostate specific membrane antigen (PSMA), (ii) administering a prostate cancer agent to the subject, and (iii) isolating circulating tumor cells obtained from a subject determined to have prostate cancer at a second time point and assaying for the ratio of prostate specific antigen (PSA) to prostate specific membrane antigen (PSMA), and (iv) comparing the ratio of PSA/PSMA measured at the second time point to the ratio of PSA/PSMA measured at the first time point, wherein if the ratio at the second time point is decreased compared to the ratio at the first time point, identifying the individual as being responsive to the prostate cancer treatment.

50. The method of paragraph 49, wherein the first time point is prior to initiation of the treatment for prostate cancer.

51. The method of paragraph 49, wherein the first time point is after discontinuation of a hormone therapy.

52. The method of paragraph 49, wherein the circulating tumor cells are isolated using a microfluidic capture method.

53. The method of paragraph 49, wherein the subject is being treated with bicalutamide, MVD3100, abiraterone acetate, cabazitaxel, sipulecel T, ketoconazole, TAK-700, or a taxane chemotherapeutic agent.

54. The method of paragraph 49, wherein the subject is being treated with a hormone therapy for prostate cancer.

55. The method of paragraph 54, wherein the hormone therapy comprises leuprolide.

56. The method of paragraph 49, wherein the circulating tumor cells are isolated from a blood sample obtained from the subject.

57. The method of paragraph 49, wherein the expression levels of PSA and PSMA are determined by contacting the isolated circulating tumor cells with antibody reagents specific for PSA and PSMA.

58 The method of paragraph 57, wherein the expression levels of PSA and PSMA are determined by immunofluorescence staining and/or automated fluorescence microscopy.

59. A method of treating a patient having prostate cancer, the method comprising: (i) isolating circulating tumor cells from a biological sample obtained from a subject, (ii) determining the ratio of prostate specific antigen (PSA) to prostate specific membrane antigen (PSMA) expression, (iii) if the PSA/PSMA expression ratio is increased compared to that of a reference value, administering to the subject a prostate cancer agent that has not been previously administered to the subject.

EXAMPLES

Prostate cancer is initially responsive to androgen deprivation therapy (ADT), and reactivation of androgen receptor (AR) signaling in the absence of or presence of reduced levels of androgen is thought to underlie its progression to castration-resistant prostate cancer (CRPC). Despite potent new therapies targeting AR pathway components, there are no reliable biomarkers to guide their application in patients with CRPC. Here, microfluidic capture of circulating tumors cells (CTCs) was used to measure AR signaling readouts before and after therapeutic interventions. Single cell immunofluorescence analysis revealed predominantly "AR-on" CTC signatures in untreated patients, compared to heterogeneous CTC populations in patients with CRPC. Initiation of first line ADT induced a profound switch from "AR-on" to "AR-off" CTCs, whereas secondary hormonal therapy in CRPC resulted in variable responses. An increase in "AR-on" CTCs despite treatment with abiraterone acetate was correlated with shorter time to treatment discontinuation. Together, these studies demonstrate that treatment-induced signaling responses are detectable within CTCs, permitting serial measurements of drug response to guide therapy in prostate and potentially other cancers. CTCs provide a better window on sensitivity to hormonal therapy than tumor load or tumor tissue biopsy; that is, measuring the ratio of PSA/PSMA in circulating tumor cells is more predictive of hormonal resistance than measuring the expression or ratio of PSA/PSMA in whole blood, serum or in a tissue biopsy sample.

Acquired resistance to first line hormonal therapy in prostate cancer is heterogeneous in the extent of androgen receptor pathway reactivation. Measurement of pre- and post-treatment AR signaling within CTCs help target such treatments to patients most likely to respond to second line therapies.

Example 1: Background of the Study

Prostate cancer cells are highly dependent upon AR signaling for their proliferation and survival. In men with metastatic prostate cancer, androgen deprivation therapy (ADT) results in durable responses in most patients (Chen Y, et al. *Curr Opin Pharmacol* 2008; 8: 440-8). Despite high rates of initial response to ADT, disease progression is invariably observed with tumor cells resuming proliferation despite continued treatment (termed castration-resistant prostate cancer or CRPC). The propensity of metastatic prostate cancer to spread to bone has limited repeated sampling of tumor deposits that have acquired castration resistance, but insights into resistance mechanisms have emerged through bone marrow biopsy and autopsy studies, as well as mouse modeling experiments (Yuan X and Balk S P. *Urol Oncol* 2009; 27: 36-41).

The concept that CRPC results from reactivation of AR signaling despite low levels of serum testosterone is consistent with a frequently observed rise in serum prostate specific antigen (PSA), an androgen-responsive gene product secreted into the blood by prostate cancer cells (Yuan X and Balk S P. *Urol Oncol* 2009; 27: 36-41; Scher H I and Sawyers C L. *J Clin Oncol* 2005; 23: 8253-61). Potential mechanisms by which AR reactivation occurs in CRPC include variable levels of AR gene amplification (~30% of cases) (Visakorpi T et al. *Nat Genet* 1995; 9: 401-6; Brown R S et al. *J Pathol* 2002; 198: 237-44), activating AR mutations (Taplin M E et al. *J Clin Oncol* 2003; 21: 2673-8), or alternative mRNA splicing (~10%) (Dehm S M et al. *Cancer Res* 2008; 68: 5469-77). More rarely reported are increased expression levels (Gregory C W et al. *Cancer Res* 2001; 61: 4315-9) or activation (Gregory C W et al. *J Biol Chem* 2004; 279: 7119-30) of AR transcriptional coactivators, activation of modulatory kinase pathways (e.g. Ras, PI3kinase) (Bakin R E et al. *Cancer Res* 2003; 63: 1981-9), tyrosine phosphorylation of AR itself (Guo Z et al. *Cancer Cell* 2006; 10: 309-19), and increased intratumoral androgen synthesis (Dillard P R et al. *Mol Cell Endocrinol* 2008; 295: 115-20). The functional significance of reactivated AR signaling in CRPC has been inferred from mouse xenograft models of prostate cancer, in which even modest increases in AR gene expression cause tumors to become resistant to castration therapy (Chen C D et al. *Nat Med* 2004; 10: 33-9).

The concept of AR reactivation in CRPC has become therapeutically relevant with the development of potent novel inhibitors of the AR signaling pathway (Tran C et al. *Science* 2009; 324: 787-90; de Bono J S et al. *N Engl J Med* 2011; 364: 1995-2005). The demonstration that abiraterone acetate, a CYP17A1 inhibitor that potently suppresses adrenal and intratumoral steroid biosynthesis, increases overall survival in men with metastatic CRPC who have previously received chemotherapy lends support to the rationale of suppressing AR reactivation in CRPC (de Bono J S et al. *N Engl J Med* 2011; 364: 1995-2005). Notably, there is a wide variation in patient response to abiraterone acetate as measured by serum PSA (de Bono J S et al. *N Engl J Med* 2011; 364: 1995-2005), and there is an unmet need for reliable biomarkers that can predict treatment response to abiraterone acetate and other potent inhibitors of AR signaling under development. Taking advantage of recent technological advances in the capture, imaging, and molecular characterization of rare CTCs shed into the vasculature from otherwise poorly accessible metastatic tumor deposits (Stott S L et al. *Sci Transl Med* 2010; 2: 25ra3; Stott S L, et al. *Proc Natl Acad Sci USA* 2010; 107: 18392-7), a noninvasive "real time" measure of intratumoral AR signaling was established before and after initial or second line hormonal therapy in patients with metastatic prostate cancer.

Example 2: Results

Single Cell Measurement of AR Signaling Parameters in Prostate CTCs

Figure 5:
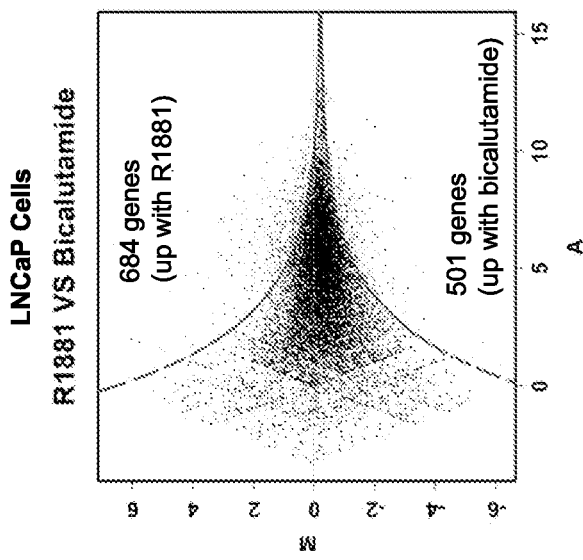
FIG. 5 shows data relating to AR transcriptional signature derivation and validation. Single molecule RNA sequencing and digital gene expression (DGE) profiling reveals differentially expressed genes in LNCaP cells treated with R1881 or bicalutamide for 24 hours. Red dots on M-A plot represent individual transcripts up-regulated with R1881 or bicalutamide (FDR<0.05). The top 24 differentially expressed genes were selected to comprise the AR transcriptional signature.

To measure the status of AR signaling within individual cells, a quantitative immunofluorescence assay was established based on the expression of AR regulated genes. It was reasoned that such a readout would be independent of mechanisms of AR reactivation in CRPC (e.g. AR amplification or mutation, ligand overexpression, or AR cofactor misregulation) and would therefore provide a clear measure of whether the AR pathway has been re-activated during the acquisition of resistance to androgen deprivation therapy. To identify optimal downstream readouts of AR signaling, a prostate cancer cell line (LNCaP cells) was subjected to androgen deprivation or stimulation, and used digital gene expression (DGE) profiling to identify transcripts that are differentially regulated in response to changes in AR signaling (FIG. 5). Among candidate gene products that are prostate cancer specific and for which reliable antibodies are available, Prostate Specific Antigen (PSA; KLK3) and Prostate Specific Membrane Antigen (PSMA; FOLH1) were selected as most consistently upregulated following AR activation and AR suppression, respectively (FIG. 1A; FIG. 5; data not shown). Selection of PSMA as a marker of AR suppression in an imaging study was also recently described by Evans et al. (Evans M J et al. *Proc Natl Acad Sci USA* 2011; 108: 9578-82).

Figure 6:
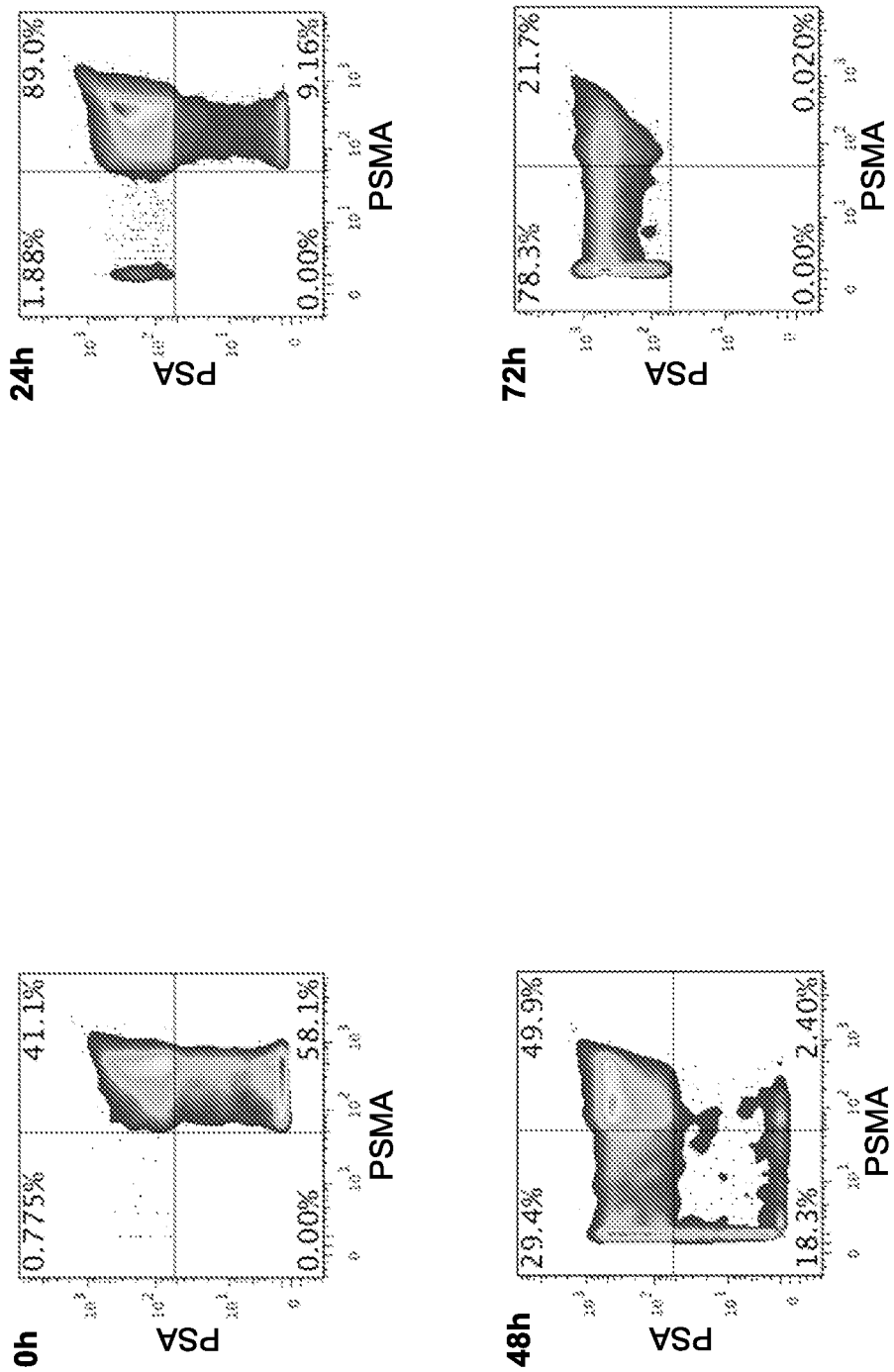
FIG. 6 shows data relating to a time course for VCaP prostate cancer cells treated with R1881. Multiparameter single cell immunofluorescence assay for AR signaling applied to VCaP prostate cancer cells after treatment with 1 nM R1881 after 3 days culture in medium containing 10% charcoal-stripped serum.

To achieve multiparameter single cell analysis of AR activity, an automated fluorescence microscopy scanning platform was adapted to distinctly and specifically measure four fluorescent emission spectra simultaneously. Secondary fluorophores and optical band pass filters were selected to avoid "cross-talk" between the multiple fluorescent signals that are closely located on the electromagnetic spectrum, while maximizing signal intensity. The disclosed assay for quantitative measurement of signal intensity profiles for cells stained with antibodies against PSA and PSMA was developed using a model cell system (LNCaP). Treatment of androgen-starved LNCaP cells with the androgen R1881 revealed time-dependent progression from an initial "AR-off" (PSA–/PSMA+) to an intermediate "AR-mixed" (PSA+/PSMA+) phenotype, and finally to an "AR-on" (PSA+/PSMA–) pattern (FIG. 1B; data not shown). The reverse progression was observed upon treatment with the AR inhibitor bicalutamide (FIG. 1C; data not shown). Similar results were observed using VCaP cells, another androgen responsive prostate cancer cell line (FIG. 6).

Figures 2A, 2B:
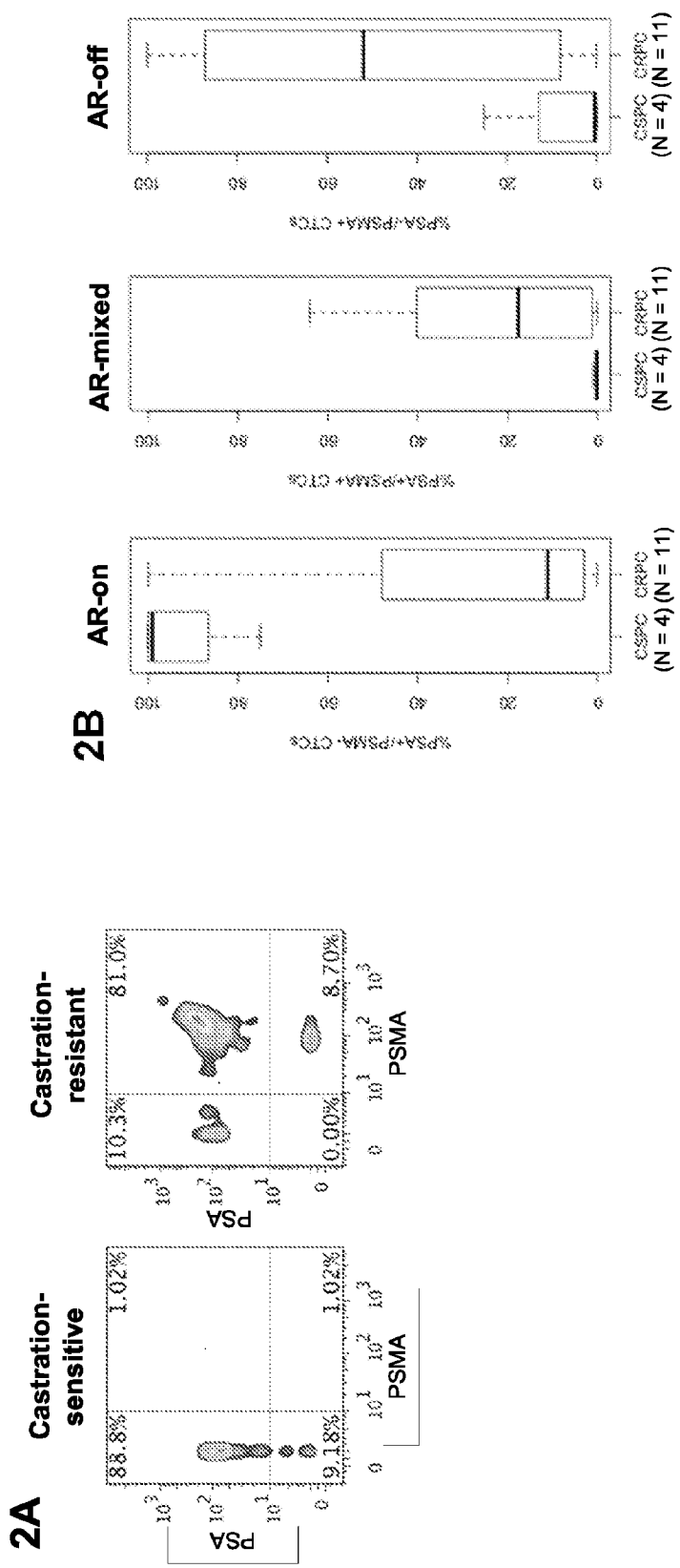
FIGS. 2A-2B show data relating to single cell measurements of AR signaling that identify predominantly AR-on CTCs in castration-sensitive prostate cancer versus heterogeneous signatures in castration-resistant prostate cancer.
Figure 7:
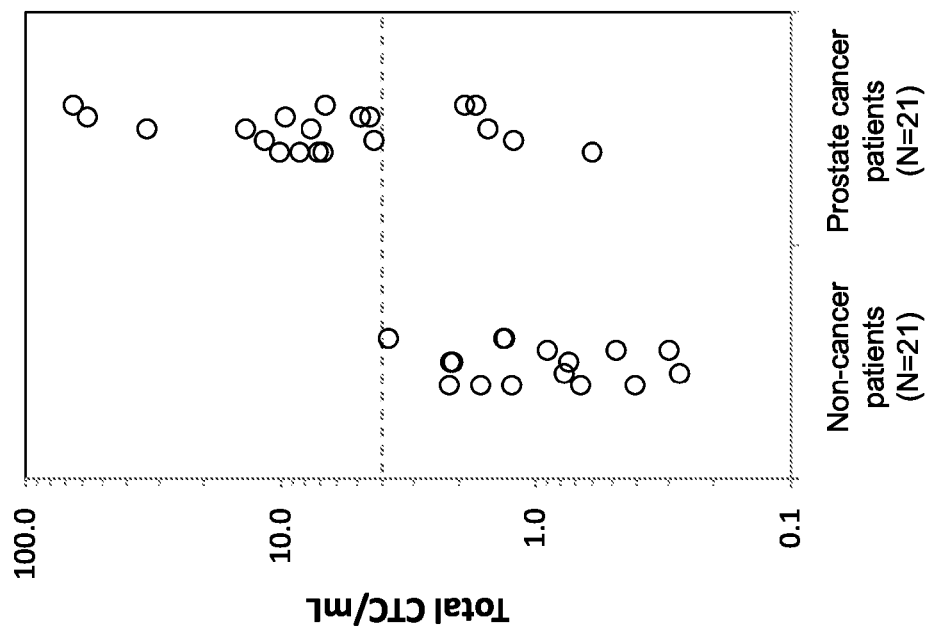
FIG. 7 shows enumeration of CTCs in metastatic prostate cancer patients (N=21) and male patients with no known diagnosis of cancer (N=21) using HBCTC-chip 4-color imaging parameters. Captured cells were stained in 4 colors with antibodies against PSA (Cy5), PSMA (Cy3), CD45 (FITC), and DAPI for DNA. Total CTC/mL refers to the sum of PSA+/PSMA−/CD45− CTC count, PSA−/PSMA+/CD45− CTC count, and PSA+/PSMA+/CD45− CTC count, divided by the total volume of blood processed. Dashed line refers to the signal intensity threshold for detection (4 CTC/mL), previously determined by analysis of healthy donor blood samples, below which a signal is considered a false positive.
Figure 8A:
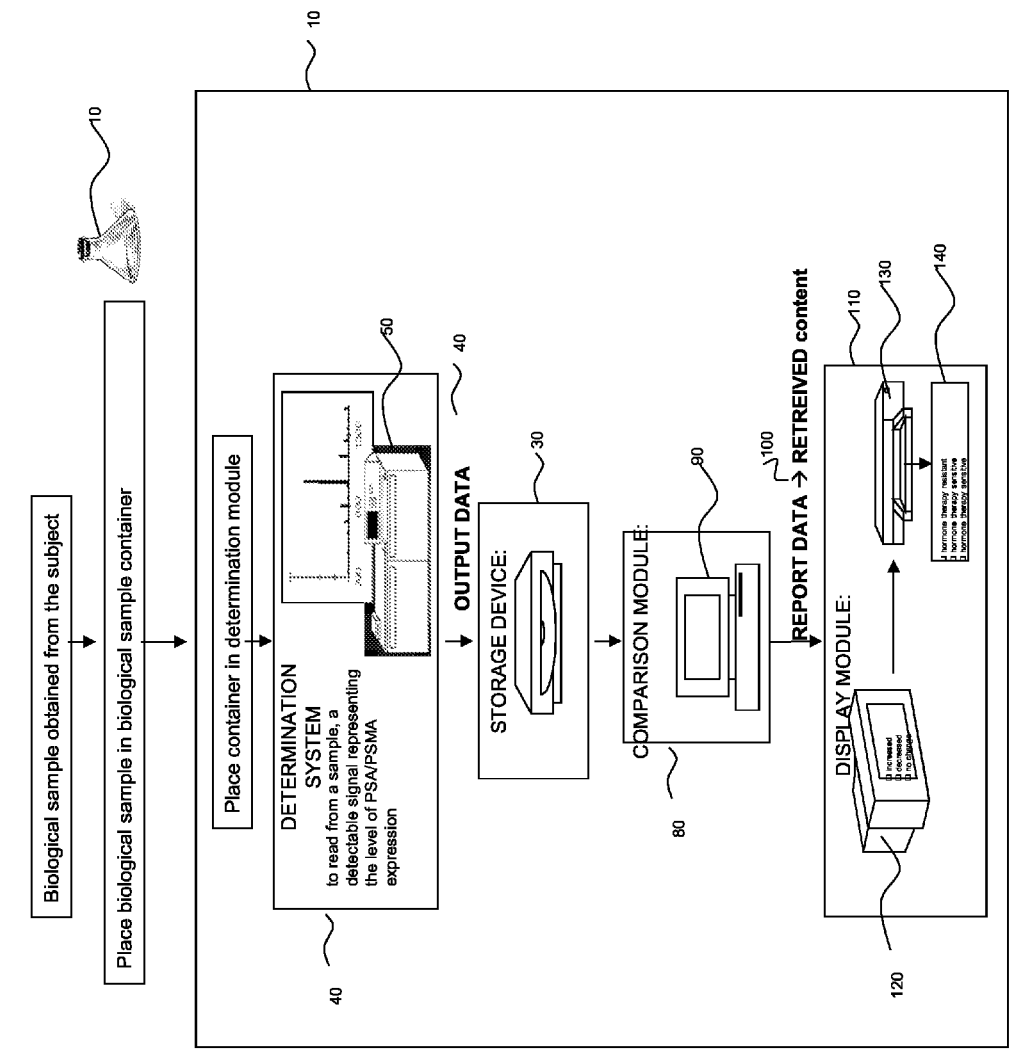
FIGS. 8A-8B are block diagrams depicting an exemplary system for use with the assays and methods described herein (FIG. 8A) and exemplary instructions encoded on a computer readable storage medium for use with the systems described herein (FIG. 8B).
Figure 8B:
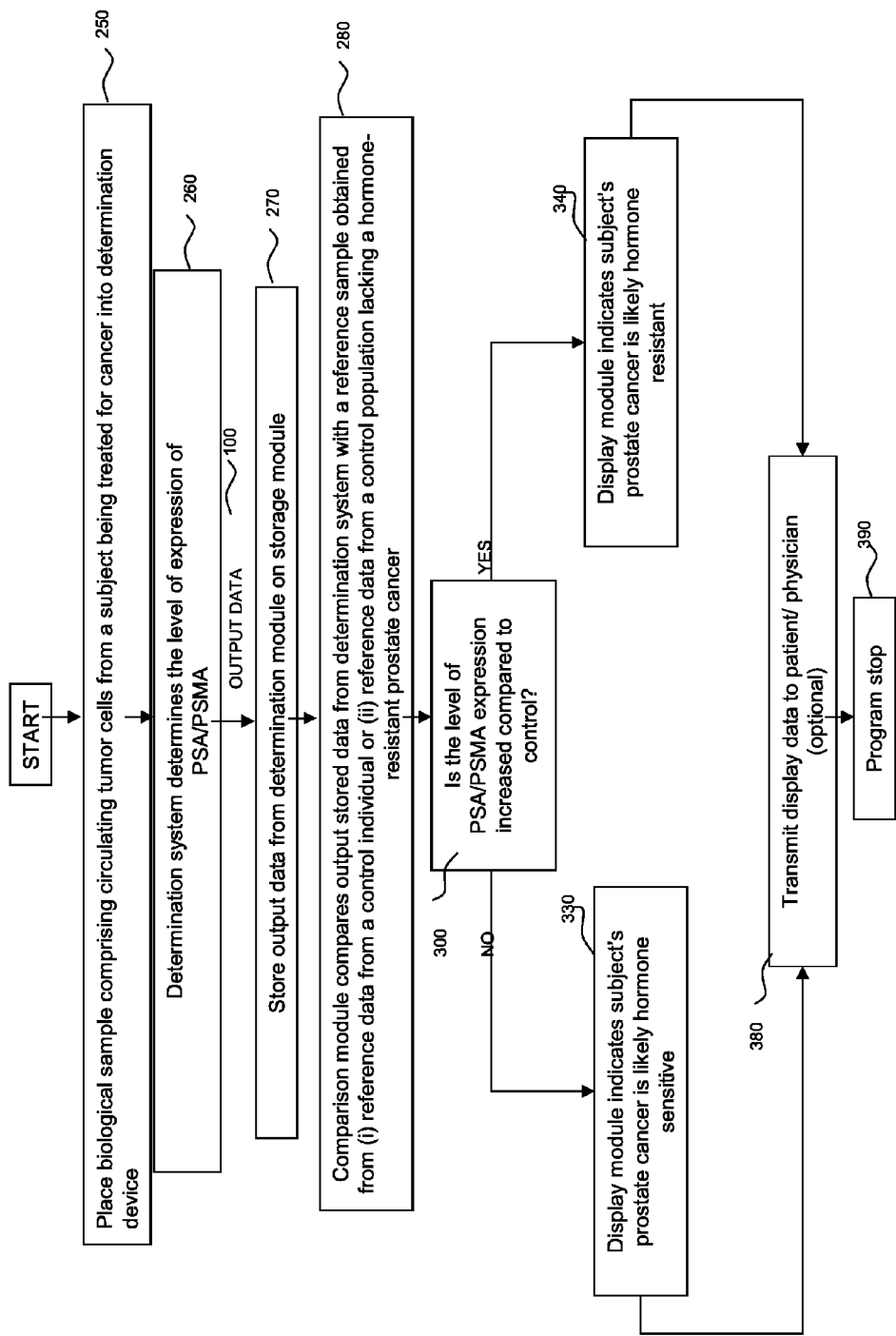

$^{HB}$CTC-Chip parameters (Herringbone Circulating tumor cell: $^{HB}$CTC) for this single cell AR signaling analysis were established by modeling LNCaP cells treated with R1881 or bicalutamide, spiked into control blood specimens, captured on the $^{HB}$CTC-Chip, and stained with antibodies against PSA and PSMA (AR signaling) along with anti-CD45 (to exclude contaminating leukocytes) and DAPI (nuclear morphology) (data not shown). The four-color immunofluorescence imaging parameters established using LNCaP cells were then applied to accurately enumerate patient-derived CTCs (FIG. 2A). Analysis of pretreatment blood samples from metastatic prostate cancer patients revealed that CTCs were detectable above the predetermined signal intensity threshold (derived from analysis of healthy controls) in 72% of patients (N=15/21) (FIG. 7). In contrast, in age-matched male patients with no known diagnosis of cancer, CTCs were detectable above threshold in 0% of patients (N=0/21) (FIG. 7).

Figure 3A:
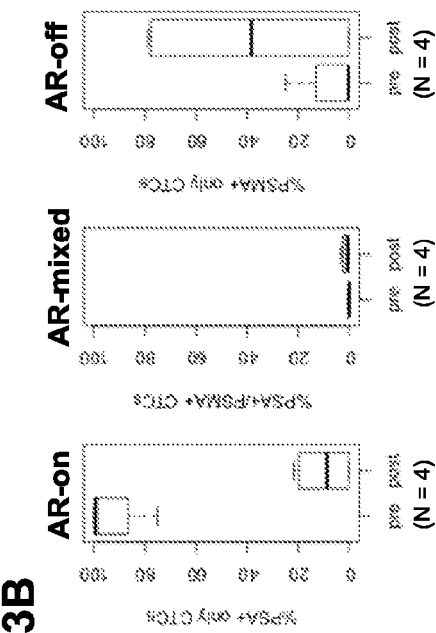
FIGS. 3A-3B show data relating to ADT-induced AR signaling changes in CTCs from patients with castration-sensitive metastatic prostate cancer.
Figure 3B:
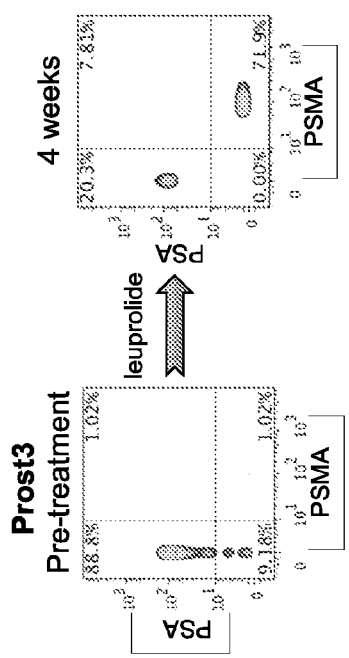

Homogeneous AR Signaling in CTCs from Untreated Patients with Metastatic Prostate Cancer CTCs were detectable in 4 of 5 (80%) patients with newly diagnosed metastatic prostate cancer prior to the initiation of androgen deprivation therapy. AR activity was predominantly positive amongst the patients with detectable CTCs, with the vast majority (median 99.1%, range 75%-100%) of isolated CTCs from each patient showing the "AR-on" (PSA+/PSMA−) phenotype (FIG. 2B; Table 1). The initiation of ADT in treatment-naïve metastatic prostate cancer patients with detectable CTCs resulted in transformation of the majority of CTCs from the "AR-on" to the "AR-off" phenotype within one month, followed by the complete disappearance of CTCs by 3 months after initiation of therapy (FIGS. 3A-3B; Table 1).

Heterogeneous AR Signaling in CTCs from Patients with CRPC

In marked contrast, CRPC patients with detectable CTCs pretreatment (N=11/16; 69%) displayed both intra-patient and inter-patient heterogeneity in CTC AR activity (FIGS. 2A-2B; Table 1). Most remarkable was the abundance within each patient of CTCs with the "AR-off" (PSA−/PSMA+) signature (median 51.9%), as well as CTCs with an "AR-mixed" (PSA+/PSMA+) phenotype (median 17.6%). Despite the expected reactivation of AR signaling in CRPC, only a relatively small fraction of CTCs in these patients had the "AR-on" (PSA+/PSMA−) phenotype (median 11.1%). In contrast to the consistent treatment induced changes in AR signaling patterns seen within CTCs of patients with CSPC, second line hormonal treatment in CRPC patients had varying effects on CTC numbers and AR phenotypes (FIGS. 4A-4D; Tables 1 and 2). This included patients treated with the relatively weak hormonal agents ketoconazole (N=1) and bicalutamide (N=2), as well as the potent CYP17A1 inhibitor abiraterone acetate (N=13) (Supplementary Table S1). Four of 13 (31%) CRPC patients treated with abiraterone acetate had a ≥50% decline in the percentage of "AR-on" CTCs within 2-5 weeks of therapy, and 6 of 13 (46%) CRPC patients had a stable percentage of "AR-on" CTCs after therapy (FIGS. 4A-4B; Tables 1 and 2), indicating that the reduction in systemic androgen levels suppressed a subset of metastatic tumor cells with reactivated AR signaling. In contrast, 3 of 13 (23%) CRPC patients had a ≥50% increase in the percentage of "AR-on" CTCs within the first 2-5 weeks of therapy with abiraterone acetate, indicating increased AR signaling despite therapy (FIGS. 4C-4D; Tables 1 and 2). Of note, an increase in the percentage of "AR-on" CTCs despite abiraterone acetate therapy was correlated with a significantly shorter time to treatment discontinuation, a marker of disease progression (logrank P=0.031; data not shown). In comparison, serum PSA response, defined as a maximal decline of ≥50% in serum PSA (Scher H I et al. J Clin Oncol 2008; 26: 1148-59), was not significantly correlated with time to treatment discontinuation (logrank P=0.447).

Discussion

Cancer cells circulating in the peripheral blood provide a uniquely accessible source of tumor-derived material for molecular analyses. In metastatic prostate cancer, which primarily spreads to bone, the inability to noninvasively sample metastatic lesions has limited the ability to individualize second line therapies according to mechanism of drug resistance. Thus, while potent new inhibitors of the AR pathway are under active development, their clinical deployment still remains empiric. Given the inter-patient variation in outcome, there is an unmet clinical need for a biomarker that can enable prediction of treatment response for individual patients. Here, it is demonstrated that the activity of the AR pathway can be monitored in CTCs. These results support the relevance of CTCs as dynamic tumor-derived biomarkers, reflecting "real time" effects of cancer drugs on their therapeutic targets, and the potential of CTC signaling analysis to identify the early emergence of resistance to therapy.

It was found that profound differences underlie the dramatic response of previously untreated, castration-sensitive disease to androgen deprivation therapy, compared with the relatively limited effectiveness of even potent second line hormonal agents in castration-resistant disease. CSPC is marked by the presence of uniform and strong "AR-on" CTC signals, with rapid switching to "AR-off" upon androgen withdrawal, preceding the disappearance of CTCs from the circulation. In contrast, CRPC is marked by striking heterogeneity among tumor cells from individual patients, as well as between different patients with similar clinical histories. Few "AR-on" cells are observed, and instead there is an abundance of both "AR-off" and "AR-mixed" CTCs. Together, these data indicate that pathways other than AR signaling contribute to disease progression in CRPC, and that the AR reactivation that does occur may be qualitatively altered despite the known overexpression of AR itself. Indeed, reactivation of AR signaling in CRPC appears not to be as complete as previously suspected, and even potent AR suppression in this setting may be insufficient by itself to mediate dramatic tumor responses. Rising serum PSA levels in patients with CRPC have been taken as evidence of strong AR reactivation and renewed susceptibility to hormonal manipulation. However, these serum measurements reflect total tumor burden, which may be considerable, whereas single cell CTC analysis suggests that within individual tumor cells, AR signaling is not fully reactivated.

While AR reactivation is the dominant model to explain acquisition of resistance to androgen withdrawal, the limited human data available are consistent with the observations noted in this study that indicate an attenuated AR phenotype in CRPC. For instance, gene expression studies of bone metastases have shown increased AR mRNA levels in CRPC (Stanbrough M et al. *Cancer Res* 2006; 66: 2815-25), and bone marrow biopsy studies (Efstathiou E *J Clin Oncol* 2011) as well as CTC analysis (Darshan M S et al. *Cancer Res* 2011; 71: 6019-29) have demonstrated nuclear AR localization (Efstathiou E *J Clin Oncol* 2011), but androgen-activated genes have been found on average to be reduced 2- to 3-fold in CRPC compared with primary untreated prostate cancer (Stanbrough M et al. *Cancer Res* 2006; 66: 2815-25; Mendiratta P et al. *J Clin Oncol* 2009; 27: 2022-9). The most common acquired genetic alteration affecting AR, a median 1.6 to 5-fold gene amplification seen in ~30% of cases (Visakorpi T et al. *Nat Genet* 1995; 9: 401-6; Brown R S, et al. *J Pathol* 2002; 198: 237-44), may not be sufficient to fully overcome the effects of ligand withdrawal and re-establish full AR-driven tumor cell proliferation. Indeed a recent analysis of gene promoters targeted by AR in cells that are sensitive to androgen withdrawal versus cells with acquired resistance has demonstrated a qualitatively distinct subset of AR activated genes (Wang Q, et al. Cell 2009; 138: 245-56; Cai C, et al. *Cancer Cell* 2011; 20: 457-71). Thus, expression analysis of downstream AR targeted genes in CTCs can provide a functionally relevant measure of overall AR activity.

In addition to altered AR signaling, other AR-independent pathways, including PIK3CA-dependent signaling, have also been implicated in CRPC and may cooperate with partial AR reactivation in mediating disease progression in prostate cancer (Carver B S, et al. *Cancer Cell* 2011; 19: 575-86). Recent studies in mouse models of CRPC have suggested improved responses to combined AR and mTOR pathway inhibition (Carver B S, et al. *Cancer Cell* 2011; 19: 575-86). Given the potentially complex and heterogeneous mechanisms underlying CRPC, it is not surprising that treatment with the potent CYP-17A1 inhibitor abiraterone acetate has a varied effect on the number and composition of CTCs. A subset of patients who did have measureable "AR-on" CTCs demonstrated a >50% decline in the percentage of this CTC subset within 2-5 weeks of abiraterone acetate therapy (4 of 13 patients; 31%). Given the mechanism of drug action, these cases may be enriched for patients in whom intra-tumoral or adrenal gland synthesis of androgens plays a major role in the development of castration-resistance. In contrast, tumors driven by ligand-independent AR gene activation would not be expected to show any suppression in "AR-on" CTC numbers. Indeed, a rising fraction of "AR-on" CTCs despite continued abiraterone acetate therapy was associated with a poor outcome, defined as a significantly shorter time to treatment discontinuation. In these patients, ligand-independent AR activity can become a driver of tumor cell proliferation, leading to therapeutic failure. Potential mechanisms for the development of resistance to abiraterone acetate in CRPC are the subject of intense investigation (Cai C et al. *Cancer Res* 2011; 71: 6503-13). Further studies linking such mechanistic insights with the application of novel therapies targeting the relevant pathways can provide critical guidance in molecularly targeted therapy for CRPC.

In summary, the PSA/PSMA-based AR signaling assay in CTCs described herein permits real time quantitative monitoring of intra-tumoral AR signaling and its potential contribution to disease progression within an individual patient. While this study was in progress, PET imaging using radio-labeled antibodies against PSMA and PSA were reported as biomarkers of androgen receptor signaling in prostate cancer mouse xenografts treated with the investigational AR inhibitor MDV 3100 (Evans M J, et al. *Proc Natl Acad Sci USA* 2011; 108: 9578-82; Ulmert D, et al. *Cancer Discovery* 2012; 2: 320-7). If successful in human tumor imaging, radioisotope scanning for AR activity can complement single cell CTC assays in providing ongoing monitoring for second line hormonal agents in CRPC. Such individualization of second line treatments in metastatic prostate cancer is useful to improve therapeutic success, given the evident tumor cell heterogeneity that accompanies the emergence of resistance to initial androgen deprivation.

Example 3: Methods and Materials

Patients and Clinical Specimens

Patients with metastatic prostate cancer receiving treatment at the Massachusetts General Hospital (MGH) were recruited according to an institutional review board (IRB) approved protocol. A total of 21 prostate cancer patients donated 10-20 mL of blood on one or more occasions for CTC analysis. A total of 21 male patients with no known diagnosis of cancer were recruited during routine visits to the MGH outpatient internal medicine clinic according to a separate IRB approved protocol. CTC capture using the $^{HB}$CTC-Chip was performed as described (Stott S L, et al. *Proc Natl Acad Sci USA* 2010; 107: 18392-7), with anti-EpCAM mediated capture of cells, followed by combined staining with anti-PSA, anti-PSMA, and anti-CD45 antibodies (described in detail below).

Cell Lines

LNCaP cells (ATCC) were maintained at 37° C. in 5% $CO_2$ in RPMI-1640 medium supplemented with 2 mM L-glutamine (Invitrogen), 10% fetal bovine serum (Invitrogen), and 1% penicillin-streptomycin (Invitrogen). VCaP cells (ATCC) were maintained at 37° C. in 5% $CO_2$ in DMEM high glucose medium supplemented with 2 mM L-glutamine (Invitrogen), 10% fetal bovine serum (Invitrogen), and 1% penicillin-streptomycin (Invitrogen). For generation and validation of the AR signature, LNCaP or VCaP cells were cultured for 3 days in medium supplemented with 10% charcoal-stripped fetal bovine serum (Invitrogen), and then treated with varying concentrations of R1881 (Perkin-Elmer), bicalutamide (Sigma), or DMSO as a vehicle control for varying periods of time. A Shandon Cytospin centrifuge was used to prepare cytospins of cell lines on glass slides.

$^{HB}$CTC-Chip Device Fabrication Microfluidic $^{HB}$CTC-Chip devices were made of PDMS bonded to glass substrates using soft lithography techniques, as previously described (Stott S L, et al. *Proc Natl Acad Sci USA* 2010; 107: 18392-7). The microfluidic devices were functionalized with epithelial cell adhesion molecule antibody (EpCAM, R&D Systems) or normal goat IgG irrelevant control antibody (R&D Systems) using avidin-biotin chemistry, using a previously described method (Stott S L, et al. *Proc Natl Acad Sci USA* 2010; 107: 18392-7).

HBCTC-Chip Blood Processing

All specimens were collected into Vacutainer (Becton-Dickson) tubes containing the anticoagulant EDTA and were processed through the $^{HB}$CTC-Chip within 6 hours of blood draw. Samples were run on the previously described microfluidic processing machine (Stott S L, et al. *Proc Natl Acad Sci USA* 2010; 107: 18392-7). Briefly, a 5 mL aliquot of blood was placed in an airtight conical tube on a rocker assembly, and 2~4 mL of blood were pneumatically driven through the chip at a flow rate of 1-1.5 mL/hour. Following processing, the $^{HB}$CTC-Chip was flushed with 2.5 mL of PBS at 2.5 mL/hour to remove nonspecifically bound cells. Isolated CTCs were then subjected to immunofluorescence staining, as described below.

Immunofluorescence Staining and Automated Fluorescence Microscopy

To establish and validate the immunofluorescence single cell AR signature, LNCaP cells were cultured in media containing 10% charcoal-stripped serum for 3 days followed by treatment with 1 nM R1881 or 10 µM bicalutamide for 24 hours. Once the assays were validated in cultured cells, they were applied to cells spiked into whole blood and isolated on the CTC-Chip, to healthy donor blood samples to establish the signal intensity threshold for detection, and ultimately on primary patient samples processed through the Chip. Cells captured on the $^{HB}$CTC-chip were fixed with 4% formaldehyde and permeabilized with 1% NP-40 in PBS. Immunofluorescence staining was performed using a rabbit polyclonal anti-PSA antibody (DAKO), a mouse monoclonal IgG1 anti-PSMA antibody (J591; N. Bander), and a mouse monoclonal IgG2a anti-CD45 antibody (Abcam), followed by appropriately matched secondary antibodies conjugated with DyLight 649 (Jackson ImmunoResearch), Alexa Fluor 555 (Invitrogen), and Alexa Fluor 488 (Invitrogen). Nuclei were stained with DAPI. An automated upright fluorescence microscopy scanning system (BioView) fitted with a precision motorized stage and xenon arc lamp (Lumen 2000, Prior Scientific) was used to comprehensively image each CTC-chip under 10× magnification in seven z-planes. Due to inherent auto fluorescence of biological samples that can interfere with the specificity of stains in the green spectra, the negative control marker, CD45, was paired with the Alexa Fluor 488 secondary antibody. This choice reduced the sensitivity of the staining assay (potentially more false negatives), but lessened the risk of false positives through natural autofluorescence. Conversely, PSA, the highest affinity antibody tested (and subsequently strongest fluorescent signal) was placed in the Cy5 channel, where the quantum efficiency of traditional monochrome CCD sensors is reduced. To successfully achieve distinct, non-overlapping fluorescent signals in four colors while maximizing the fluorescent intensity output, modified Magnetron sputter-coated filter sets were selected for the Cy3 and Cy5 spectra (Chroma). Additional filter sets for the DAPI and FITC channel were used and exposure times were optimized. All samples were subsequently imaged at predetermined exposure times. Potential CTC targets were automatically classified using a previously described algorithm based on predetermined fluorescence intensity and cell morphology criteria (Stott S L et al. *Sci Transl Med* 2010; 2: 25ra3), followed by manual validation by a blinded human reviewer. CTC counts were tabulated based on the total number of cells that were positive for PSA and/or PSMA, and negative for CD45. Normalized counts (CTC/mL) were calculated by dividing the total CTC count by the total volume of blood processed. Based on analysis of blood from healthy donors, a signal intensity threshold of detection was determined to be 4 CTC/mL, and normalized counts which fell below this threshold were considered to be false positive events and were not included in the final analysis. High resolution immunofluorescence images were obtained using an upright fluorescence microscope (Eclipse 90i, Nikon) under 60× magnification.

Quantitative Single Cell Immunofluorescence Analysis

Quantitative fluorescence intensity data for four different emission spectra (DAPI, FITC, Cy3, and Cy5) were obtained for each single cell, as determined by the "G-Area pixels" (FITC; CD45), "R-Area pixels" (CY5; PSA), and "Gold-Area pixels" (Cy3; PSMA) columns in the Research Mode of the Bioview image analysis software (Bioview). Data files were converted to CSV format using Microsoft Excel, and then to flow cytometry FCS format using Text-ToFCS version 1.2.1. The converted data were then analyzed using FlowJo software version 7.6. Displayed pseudocolor density plots were gated to only display events that are CD45 negative. Bar graphs were generated using Microsoft Excel, and reflect the proportions of PSA+/PSMA−/CD45−, PSA+/PSMA+/CD45−, and PSA−/PSMA+/CD45− CTCs tabulated after manual validation. Any sample with a normalized CTC count of <4 CTC/mL was considered to have a CTC count below the limit of reliable detection, based on background staining threshold previously determined from experiments processing healthy donor normal blood with the $^{HB}$CTC-Chip. In cases where normalized CTC counts were below the limit of reliable detection, percentage distributions of AR signaling phenotypes were not calculated, and "NA" was listed in Supplemental Table 51 under the corresponding columns.

Statistical Analysis

AR activity and the proportion of CTC phenotypes between samples were compared using the Wilcoxon rank-sum test. Two-sided P-values<0.05 were considered statistically significant. Treatment time was measured from the date of the start of therapy to the date of treatment discontinuation or last follow-up. Survival curves were generated using the Kaplan-Meier method and compared using the log-rank test. All statistical analyses were performed using R, version 2.12.0.

Example 4: Single Cell RNA Expression in CTCs

Figures 9A, 9B, 9C:
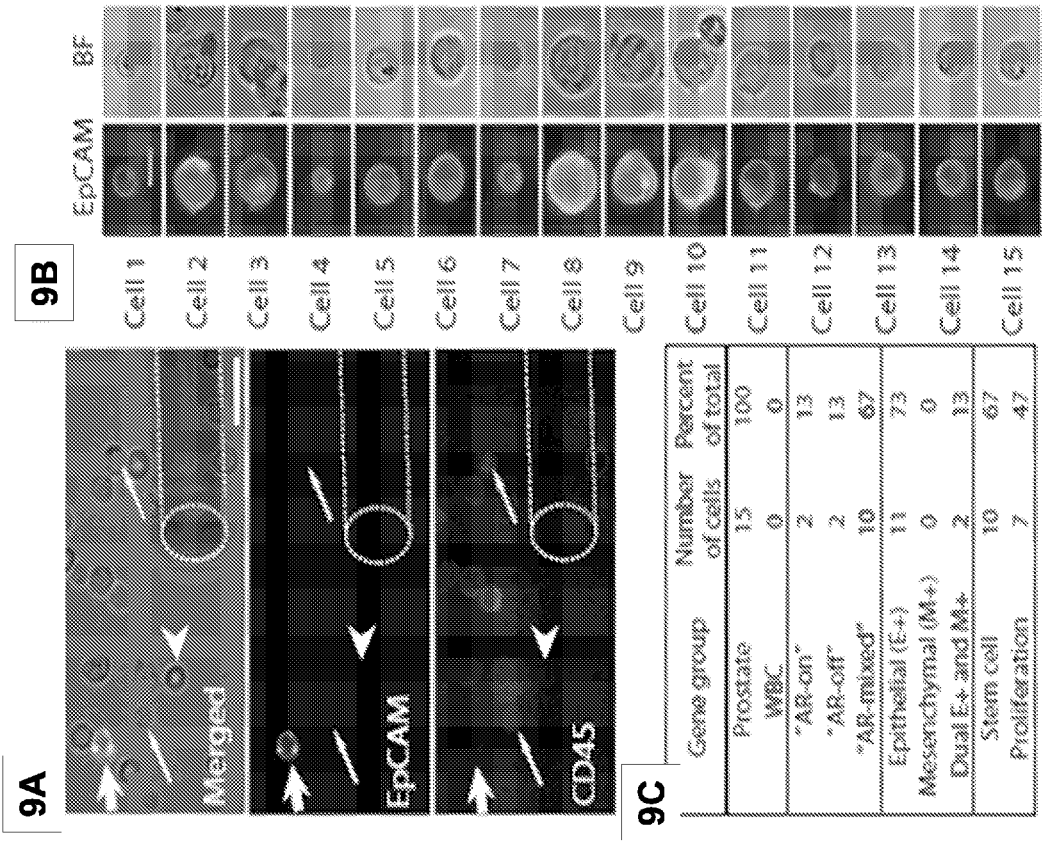
FIGS. 9A-9C demonstrate the heterogeneity of RNA expression between CTCs isolated from a prostate cancer patient

Global CTC expression analyses may identify major pathways involved in metastasis (20), but the inherent heterogeneity of CTCs necessitates the identification of expression patterns and signaling pathways within individual cells. We therefore applied single cell micromanipulation approaches to interrogate individual CTCs isolated from a patient with prostate cancer using the $^{neg}$CTC-iChip. Although micromanipulation approaches require expertise and are time-consuming, unaltered CTCs isolated rapidly with $^{neg}$CTC-iChip present high RNA quality and are in ideal condition to undergo accurate RNA-based expression profiling. We distinguished CTCs from contaminating leukocytes within the $^{neg}$CTC-iChip product by immunostaining using anti-EpCAM versus anti-CD45 antibodies (FIGS. 9A-9B). CTCs identified as EpCAM+/CD45− were individually isolated and subjected to RNA analysis by multi-gene microfluidic qRT-PCR, profiling for a panel of transcripts implicated in androgen receptor (AR) signaling, cellular proliferation, stem cell, epithelial and mesenchymal cell fates, and leukocyte-specific lineage (data not shown). Single cells from a human prostate cancer cell line (LNCaP) were used to optimize assay conditions (data not shown).

A striking heterogeneity was apparent among 15 CTCs isolated from a single patient with metastatic CRPC who had progressed through multiple lines of therapy, including androgen deprivation therapy with leuprolide, the chemotherapeutic drug docetaxel, and the second line androgen biosynthesis inhibitor abiraterone acetate. Consistent with EpCAM-positive immunostaining, most CTCs (13/15 analyzed, 87%) were positive for epithelial gene expression, of which 2 CTCs (13%) were dual positive for epithelial as well as mesenchymal markers (vimentin and N-cadherin) (FIG. 9C). Thus, a subset of CTCs appears to have undergone a partial EMT. CTC heterogeneity was also evident with expression of stem cell markers [Nanog, Oct-4 (POU5F1), c-Myc] in 10 CTCs (67%), which overlapped primarily with epithelial markers within individual CTCs (data not shown). Proliferation markers Cyclin B, Cyclin D, Aurora A kinase, and MYBL2 were detected in another subset of 7 CTCs (47%).

AR activity, previously defined in CTCs as the ratio of androgen-driven prostate specific antigen (PSA) to androgen-repressed prostate specific membrane antigen (PSMA) expression (21), was heterogeneous among CTCs. The "AR on" phenotype (PSA expression only) was only seen in 2/15 CTCs (13%), whereas the "AR-off" state (PSMA only) was evident in 2 CTCs (13%), and a "mixed AR" state (PSA+/PSMA+) in 10 CTCs (67%) (FIG. 9C). This distribution is concordant with single-cell immunofluorescence analysis of AR signaling status in CTCs from patients with CRPC (21).

Methods: Single-Cell Micromanipulation and Fluidigm qRT-PCR.

Blood samples from a patient with metastatic prostate cancer were processed through the $^{neg}$CTC-iChip, and unfixed CTCs and contaminating leukocytes were stained in solution with fluorophore conjugated antibodies against EpCAM and CD45. Single CTCs were identified based on an EpCAM+/CD45− phenotype, transferred under direct microscopic visualization to individual PCR tubes using a TRANSFERMAN NK2™ micromanipulator (Eppendorf AG). Single cell cDNA was prepared and amplified for single cell transcriptome analysis, followed by specific target pre-amplification (Fluidigm Corporation). Microfluidic qRT-PCR was performed using the BioMark Real-Time PCR system (Fluidigm Corporation). The normalized gene expression in each cell ($-\Delta C_t$) was calculated as the negative of the difference between the $C_t$ value for each gene and the GAPDH $C_t$ value for the cell. Heatmaps of normalized gene expression ($-\Delta C_t$) were generated using the HeatMapImage module of GENEPATTERN™, with global color normalization.

REFERENCES

20. M. Yu, A. Bardia, B. Wittner, S. Stott, M. Smas, D. Ting, S. Isakoff, J. Ciciliano, M. Wells, A. Shah, K. Concannon, M. Donaldson, L. Sequist, E. Brachtel, D. Sgroi, J. Baselga, S. Ramaswamy, M. Toner, D. Haber, and S. Maheswaran, "Circulating breast tumor cells exhibit dynamic changes in epithelial and mesenchymal composition.," *Science*, 339, 580-584 (2013).
21. D. T. Miyamoto, R. J. Lee, S. L. Stott, D. T. Ting, B. S. Wittner, M. Ulman, M. E. Smas, J. B. Lord, B. W. Brannigan, J. Trautwein, N. H. Bander, C. L. Wu, L. V. Sequist, M. R. Smith, S. Ramaswamy, M. Toner, S. Maheswaran, and D. A. Haber, "Androgen Receptor Signaling in Circulating Tumor Cells as a Marker of Hormonally Responsive Prostate Cancer," *Cancer Discovery*, 2, 995-1003 (2012).

The invention claimed is:

1. A method for treating prostate cancer in a patient, wherein said patient is currently being treated with first line androgen deprivation therapy (ADT), said method comprising:
   (a) isolating circulating prostate tumor cells from said patient over a period of time during which said patient is being treated with said first line ADT;
   (b) measuring the levels of expression of PSA and PSMA on the surfaces of single isolated circulating prostate tumor cells;
   (c) determining if the ratio of the levels of expression of PSA to PSMA on isolated single circulating prostate tumor cells remains the same or increases over said period of time, wherein if said ratio remains the same or increases over said period of time there is an indication that castration-resistant prostate cancer (CRPC) is emerging in said patient; and
   (d) if said ratio remains the same or increases over said period of time, then discontinuing treatment with said first line ADT and initiating treatment with a second line therapy effective to treat emerging CRPC; or
   (e) if said ratio decreases over said period of time, then continuing treatment with said first line ADT.

2. The method of claim 1, wherein said first line ADT comprises administering to the patient leuprolide.

3. The method of claim 1, wherein said second line therapy comprises administering to the patient a therapeutically effective amount of abiraterone acetate.

4. The method of claim 1, wherein said second line therapy comprises administering to the patient a therapeutically effective amount of an anti-cancer agent that has not been previously used to treat said prostate cancer in said patient.

5. The method of claim 1, further comprising treating emerging CRPC with a therapeutically effective amount of one or more additional chemotherapeutic agents.

6. The method of claim 5, wherein said one or more additional chemotherapeutic agents is selected from the group consisting of paclitaxel, docetaxel, and cabazitaxel.

7. The method of claim 1, wherein said period of time ranges from 2 weeks to 20 years.

8. The method of claim 1, wherein the steps (a)-(d) are repeated over said period of time every week, month, or year.

* * * * *

UNITED STATES PATENT AND TRADEMARK OFFICE
CERTIFICATE OF CORRECTION

PATENT NO. : 9,766,244 B2
APPLICATION NO. : 14/412235
DATED : September 19, 2017
INVENTOR(S) : Daniel A. Haber, Shyamala Maheswaran and David T. Miyamoto Page 1 of 1

It is certified that error appears in the above-identified patent and that said Letters Patent is hereby corrected as shown below:

In the Specification

At Column 1, Lines 17-21, please delete:
"The present application was made with Government support under Grant Number 5R01EB008047 awarded by National Institute of Biomedical Imaging and Bioengineering, National Institutes of Health. The Government has certain rights in this invention."

And insert the following:
--The present application was made with Government support under Grant Number 5R01EB008047 awarded by National Institute of Biomedical Imaging and Bioengineering, National Institutes of Health and Grant Number W81XWH-12-1-0153 awarded by the Department of Defense. The Government has certain rights in this invention.--

Signed and Sealed this
Seventeenth Day of September, 2019

Andrei Iancu
*Director of the United States Patent and Trademark Office*